(12) United States Patent
Jordan et al.

(10) Patent No.: US 9,610,440 B2
(45) Date of Patent: Apr. 4, 2017

(54) SYSTEMS, DEVICES, AND METHODS FOR TRANSDERMAL DELIVERY

(71) Applicants: Michael K Jordan, North Smithfield, RI (US); Miaoyong Cao, Warwick, RI (US); Christopher A Hobson, Westwood, MA (US); Matthew Gibson, Dexter, MI (US)

(72) Inventors: Michael K Jordan, North Smithfield, RI (US); Miaoyong Cao, Warwick, RI (US); Christopher A Hobson, Westwood, MA (US); Matthew Gibson, Dexter, MI (US)

(73) Assignee: Iontera, Inc, Norwood, MA (US)

( * ) Notice: Subject to any disclaimer, the term of this patent is extended or adjusted under 35 U.S.C. 154(b) by 225 days.

(21) Appl. No.: 14/301,055

(22) Filed: Jun. 10, 2014

(65) Prior Publication Data
US 2014/0364794 A1 Dec. 11, 2014

Related U.S. Application Data

(60) Provisional application No. 61/833,361, filed on Jun. 10, 2013, provisional application No. 61/833,353, filed on Jun. 10, 2013.

(51) Int. Cl.
*A61N 1/00* (2006.01)
*A61N 1/30* (2006.01)
(Continued)

(52) U.S. Cl.
CPC ............. *A61N 1/303* (2013.01); *A61N 1/044* (2013.01); *A61M 35/00* (2013.01);
(Continued)

(58) Field of Classification Search
CPC .............. A61M 5/315; A61M 5/31511; A61M 5/31513; A61M 5/31515;
(Continued)

(56) References Cited

U.S. PATENT DOCUMENTS 4,731,049 A * 3/1988 Parsi .................... A61N 1/0448
604/20
5,125,894 A * 6/1992 Phipps ................. A61N 1/0448
604/20

(Continued)

*Primary Examiner* — Kevin C Sirmons
*Assistant Examiner* — William Carpenter
(74) *Attorney, Agent, or Firm* — Ascentage Patent Law, LLC; Travis L. Johnson; David S. Einfeldt

(57) ABSTRACT

Disclosed herein are systems, devices, and methods for transdermal delivery of a therapeutic agent (for example, a molecule or molecules) to a therapy site. The systems, devices, and methods described herein are flexible and able to conform to the contours of a therapy site, such as the shape of a user's face. In certain approaches, the devices and systems described herein include an integrated power supply for standalone application to the therapy site. The devices, systems, and methods include flexible electrodes with integrated conductance layers and interface layers for improved stability and current distribution. In practice, the device includes at least two electrodes which are coupled to the therapy site. When the electrodes are placed at the therapy site, they are electrically coupled, thereby drawing a current from the power supply to deliver the therapeutic agent to the therapy site.

11 Claims, 12 Drawing Sheets

(51) Int. Cl.
*A61N 1/04* (2006.01)
*A61M 37/00* (2006.01)
*A61M 35/00* (2006.01)

(52) U.S. Cl.
CPC .... *A61M 2037/0007* (2013.01); *A61N 1/0436* (2013.01); *A61N 1/0496* (2013.01)

(58) Field of Classification Search
CPC ......... A61M 2005/31516; A61M 2005/31518; A61M 2005/3152; A61M 2005/31521; A61M 2005/31523; A61M 5/282; A61M 5/283; A61M 5/2425; A61M 5/2429; A61M 5/28; A61M 35/00; A61M 2037/0007; A61N 1/0448; A61N 1/0444; A61N 1/325; A61N 1/0428; A61N 1/30; A61N 1/0432; A61N 1/0496; A61N 1/0436
See application file for complete search history.

(56) References Cited

U.S. PATENT DOCUMENTS

| | | | | |
|---|---|---|---|---|
| 5,158,537 A | * | 10/1992 | Haak | A61N 1/0436 604/20 |
| 5,162,043 A | * | 11/1992 | Lew | A61N 1/0448 604/20 |
| 5,169,384 A | * | 12/1992 | Bosniak | A61N 1/044 604/20 |
| 5,795,321 A | * | 8/1998 | McArthur | A61N 1/303 604/20 |
| 6,635,045 B2 | * | 10/2003 | Carey | A61N 1/0448 424/449 |
| 7,945,320 B2 | | 5/2011 | Durand | |
| 2006/0235284 A1 | * | 10/2006 | Lee | A61B 5/14514 600/345 |
| 2006/0241548 A1 | * | 10/2006 | Fukuta | A61N 1/0444 604/20 |
| 2007/0027426 A1 | * | 2/2007 | Matsumura | A61N 1/0444 604/20 |
| 2007/0060860 A1 | * | 3/2007 | Nakayama | A61N 1/0444 604/20 |
| 2007/0093787 A1 | * | 4/2007 | Smith | A61N 1/0444 604/890.1 |
| 2009/0149800 A1 | | 6/2009 | Durand | |
| 2009/0299267 A1 | | 12/2009 | Durand | |
| 2010/0286590 A1 | | 11/2010 | Durand | |
| 2011/0092881 A1 | | 4/2011 | Durand | |
| 2013/0066255 A1 | | 3/2013 | Jordan | |

\* cited by examiner

SYSTEMS, DEVICES, AND METHODS FOR TRANSDERMAL DELIVERY

RELATED APPLICATIONS

This application claims priority from and includes in their entirety U.S. Patent Application No. 61/833,353 filed Jun. 10, 2013, and 61/833,361 filed Jun. 10, 2013.

BACKGROUND

Many approaches have attempted to deliver drugs transdermally, including microneedles, topical application of lotions, and iontophoresis. Effective delivery of therapeutic agents through the stratum corneum remains a challenge. While the use of electromotive force to deliver molecules transdermally has provided some level of success, traditional iontophoresis systems typically use equipment, such as external stimulators or other systems, which must be connected to electrodes or other delivery components. The electrodes, and therefore, the user, are tethered to equipment. These systems are particularly inadequate for areas of the body, such as the face, where tethered systems may impede a user's ability and willingness to use a drug delivery system.

In cosmetic applications, individuals typically either use lotions and creams, or resort to needle injections of therapeutic agents. Many individuals find creams less effective, but would prefer not to receive injections. Effective, standalone drug delivery systems are a challenge for these applications due to the need for the system to conform to the therapy site and be sufficiently lightweight, comfortable, and efficacious.

SUMMARY

Disclosed herein are systems, devices, and methods for transdermal delivery of a therapeutic agent, for example, a molecule or molecules, to a therapy site. The systems, devices, and methods described herein are flexible and able to conform to the contours of a therapy site, such as the shape of a user's face. Embodiments of low profile, conformal transdermal drug delivery systems may be beneficial for individuals desiring effective drug delivery therapies.

In certain approaches, the systems, devices and methods described herein include an integrated power supply for a standalone application to the therapy site. The devices, systems, and methods include flexible electrodes with integrated conductance layers and interface layers for improved stability and current distribution. In practice, the device includes at least two electrodes which are coupled to the therapy site. When the electrodes are placed at the therapy site, they are electrically coupled, thereby drawing a current from the power supply to deliver the therapeutic agent, for example, a molecule, to the therapy site.

In certain aspects, the systems, devices, and methods described herein include a power supply having a first terminal and a second terminal, a first electrode having a first interface layer integrally coupled to a first conductance layer, and a second electrode having a second interface layer integrally coupled to a second conductance layer. The first conductance layer is electrically coupled to the first terminal of the power supply and the second conductance layer is electrically coupled to the second terminal of the power supply. The first electrode, second electrode, and power supply are coupled to the base. The first electrode and second electrode are spaced apart by a separation channel.

The first conductance layer may have a higher electrical conductivity than the first interface layer and the second conductance layer may have a higher electrical conductivity than the second interface layer. In certain approaches, the first conductance layer and second conductance layer each comprise at least one of silver, silver chloride, carbon, aluminum, zinc, nickel, copper, gold, and platinum. In certain approaches, the first interface layer and the second interface layer each comprise at least one of vinyl, carbon, carbon-impregnated vinyl, silver, silver chloride, aluminum, zinc, nickel, gold, and platinum.

In certain approaches, the first conductance layer is a printed conductance layer on the first interface layer and the second conductance layer is a printed conductance layer on the second interface layer. Additionally or alternatively, the first conductance layer may be an extruded conductance layer on the first interface layer and the second conductance layer may be an extruded conductance layer on the second interface layer. In certain embodiments, the first conductance layer is adhesively coupled to the first interface layer and the second conductance layer is adhesively coupled to the second interface layer.

In certain embodiments, the systems, devices, and methods described herein include a power supply which is flexible. The power supply may be a battery. In certain embodiments, the power supply spans the separation channel. In certain approaches, multiple power supplies are included. The systems, devices, and methods may include a retention layer for positioning and retaining the power supply. In certain approaches, the retention layer includes a recess, and the battery is positioned within the recess. The retention layer may have a first side coupled to the base and a second side coupled to the first electrode and the second electrode.

In certain embodiments, the systems, devices, and methods described herein include conductive tape that electrically couples the first terminal of the power supply to the first conductance layer of the first electrode and the second terminal of the power supply to the second conductance layer of the second electrode. The conductive tape may comprise a first piece coupled to the first terminal and the first conductance layer, and the second piece coupled to the second terminal and the second conductance layer. In certain approaches, the conductive tape spans the separation channel. In certain embodiments, the conductive tape is anisotropic conductive tape.

In certain embodiments, the systems, devices, and methods described herein include a first coupling layer coupled to the first interface layer and a second coupling layer coupled to the second interface layer, wherein the first coupling layer and second coupling layer are spaced apart by the separation channel. The first coupling layer and second coupling layer may each include at least one of a gel, hydrogel, foam, sponge, and mesh.

In certain embodiments, the systems, devices, and methods described herein include a spacing layer coupled to the base and the power supply. The base may have an upper textured surface. In certain approaches, the systems, devices, and methods described herein include an electronics layer. For example, the power supply may be included in the electronics layer. The electronics layer may be flexible. Additionally or alternatively, the electronics layer may be stretchable. In certain approaches, the device includes a microcontroller, in electrical communication with the first electrode and second electrode, configured to deliver a current.

In certain approaches, the base has a contour configured to adapt to the anatomy of a user. For example, the contour may be a convex edge configured to partially surround the corner of an eye. The contour may include an apex configured to adapt to the brow region of a user. In certain embodiments, the first electrode and second electrode are contoured to correspond to the edge of the base. In certain approaches, the first electrode and second electrode are flexible. In certain approaches, the base is flexible. In certain embodiments, the systems, devices, and methods described herein include a third electrode.

In certain aspects, the systems, devices, and methods described herein include a kit for transdermal delivery of a therapeutic agent, for example, a molecule, to a therapy site. For example, the kit may include a device for transdermal delivery and a serum with a therapeutic agent, for example, a molecule. In certain aspects, the device includes a power supply having a first terminal and a second terminal, a first electrode having a first interface layer integrally coupled to a first conductance layer, and a second electrode having a second interface layer integrally coupled to a second conductance layer. The first conductance layer is electrically coupled to the first terminal of the power supply and the second conductance layer is electrically coupled to the second terminal of the power supply. The first electrode, second electrode, and power supply are coupled to the base. The first electrode and second electrode are spaced apart by a separation channel.

In certain aspects, methods are provided for delivering a therapeutic agent, for example, a molecule, to a therapy site. The method includes providing a flexible delivery device having a power supply, a first electrode, and a second electrode, wherein the first electrode and second electrode are spaced apart by a separation channel; applying a serum containing a therapeutic agent, for example, a molecule, to a therapy site; and placing the first electrode and the second electrode on the therapy site to electrically couple the first electrode and the second electrode, thereby drawing a current from the power supply to deliver the therapeutic agent, for example, a molecule, to the therapy site.

In certain approaches, the therapeutic agent, for example, a molecule, has a non-neutral charge. The first electrode may have a first interface layer integrally coupled to a first conductance layer, wherein the first conductance layer is electrically coupled to a first terminal of the power supply. The second electrode has a second interface layer integrally coupled to a second conductance layer, wherein the second conductance layer is electrically coupled to a second terminal of the power supply.

In certain embodiments, the method includes flexing the delivery device to conform to the shape of the therapy site. The method may also include adhering the delivery device to the therapy site. In certain approaches, the power supply, first electrode, and second electrode of the delivery device are coupled to an upper base layer. The first electrode may have a first coupling layer and the second electrode may have a second coupling layer, wherein the first coupling layer and second coupling layer contact the therapy site when the first electrode and second electrode are placed on the therapy site. In certain embodiments, the delivery device includes a third electrode, and placing the first electrode and the second electrode on the therapy site includes placing the third electrode on the therapy site. The third electrode may have a third coupling layer, wherein the third coupling layer contacts the therapy site when the third electrode is placed on the therapy site.

Variations and modifications of these embodiments will occur to those of skill in the art after reviewing this disclosure. The foregoing features and aspects may be implemented, in any combination or sub-combination, including multiple dependent combinations and sub-combinations, with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION OF PREFERRED EMBODIMENT

Disclosed herein are systems, devices, and methods for transdermal delivery of a therapeutic agent, for example, a molecule or molecules, to a therapy site. The systems, devices, and methods described herein are flexible and able to conform to the contours of a therapy site, such as the shape of a user's face. In certain approaches, the devices and systems described herein include an integrated power supply for standalone application to the therapy site. The devices, systems, and methods include flexible electrodes with integrated conductance layers and interface layers for improved stability and current distribution. In practice, the device includes at least two electrodes which are coupled to the therapy site. When the electrodes are placed at the therapy site, they are electrically coupled, thereby drawing a current from the power supply to deliver the therapeutic agent, for example, a molecule, to the therapy site.

In certain aspects, the systems, devices, and methods include a power supply having a first terminal and a second terminal, a first electrode having a first interface layer integrally coupled to a first conductance layer, and a second electrode having a second interface layer integrally coupled to a second conductance layer. The first conductance layer is electrically coupled to the first terminal of the power supply and the second conductance layer is electrically coupled to the second terminal of the power supply. The first electrode, second electrode, and power supply are coupled to the base. The first electrode and second electrode are spaced apart by a separation channel.

To provide an overall understanding of the systems, devices, and methods described herein, certain illustrative embodiments will be described. Although the embodiments and features described herein are specifically described for use in connection with transdermal delivery systems for delivery of therapeutic agents, for example, molecules, to a therapy site applied to a portion of the face, it will be understood that all the components, connection mechanisms, adjustable systems, manufacturing methods, and other features outlined below may be combined with one another in any suitable manner and may be adapted and applied to medical devices and procedures for other applications, including, but not limited to delivery of cosmetic agents, pharmaceutical agents, vitamins, biological agents, antibiotics, steroids, antibodies, proteins, peptides, and nutritional supplements. Examples of therapeutic agents may include an ionic therapeutic molecule, a charged therapeutic molecule, a peptide, a vitamin, a plant extract, any other therapeutic molecule, or any combination of therapeutic molecules.

Figure 1A:
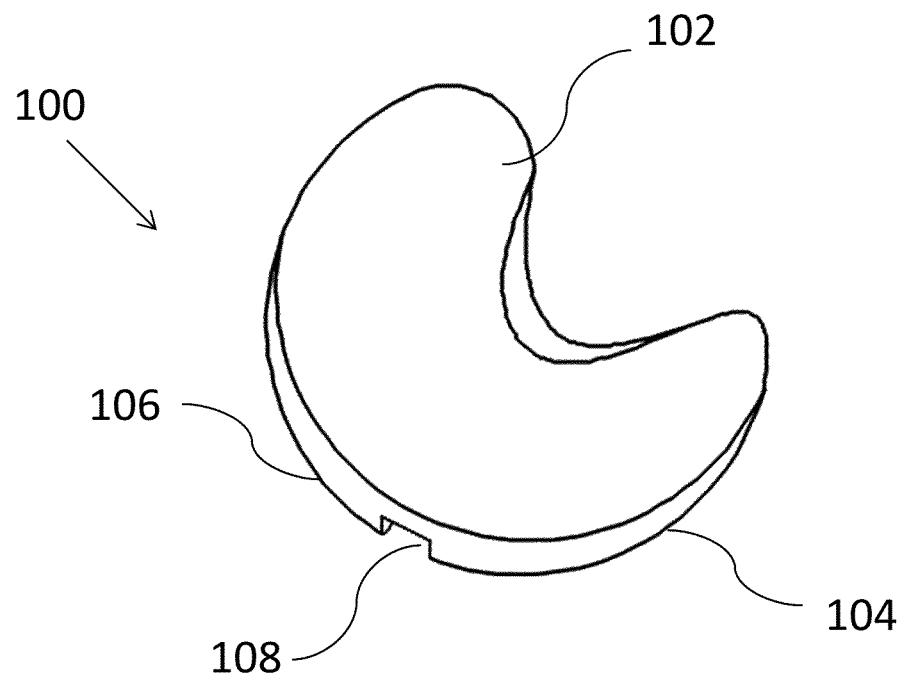
FIG. 1A depicts a top perspective view of an embodiment of a transdermal drug delivery device.
Figure 1B:
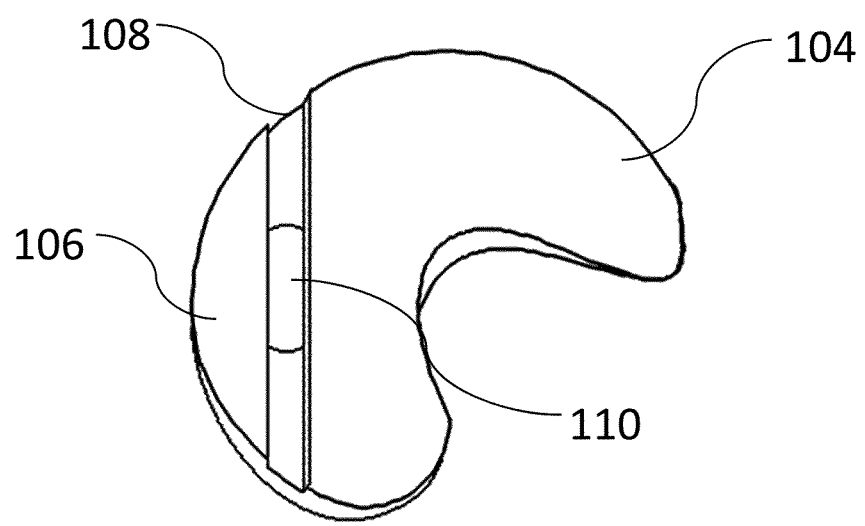
FIG. 1B depicts a bottom perspective view of an embodiment of a transdermal drug delivery.

FIG. 1A depicts a top perspective view of a transdermal drug delivery device 100 for transdermal drug delivery, and FIG. 1B depicts a bottom perspective view of device 100. Device 100 is placed on the skin for delivering therapeutic agents, for example, molecules, to a therapy site. For example, device 100 may be used for delivering molecules for treating wrinkles on the face, such as around the eye, for example, to treat "crow's feet", or on the forehead. The device 100, as well as other systems, devices, and methods described herein, provide an improvement over traditional approaches of drug delivery, such as topical lotions and needle-based injections. As will be described in further detail below, the systems, devices, and methods described herein, such as device 100, can be applied to regions, such as the face, with complex shapes and contours. The device 100 is a standalone system with an integrated power supply to avoid the use of wires or other undesired parts of typical electrical-based drug delivery systems. The device 100, as well as the other systems and devices described herein, is sufficiently lightweight and comfortable for application to the face.

The device 100 includes an upper surface 102. In certain approaches, upper surface 102 may include texturing to improve a user's ability to apply device 100 to a portion of the body. For example, the texturing may provide friction, which allows the user to effectively press and apply device 100 on a therapy site. The device 100 includes a first contact surface 104 and a second contact surface 106, which are placed on the skin when device 100 is in use. The first contact surface 104 and the second contact surface 106 may include electrodes, gels, and other components for drug delivery as described in further detail herein. The first contact surface 104 and the second contact surface 106 are spaced apart by separation channel 108. The separation channel 108 keeps first contact surface 104 and second contact surface 106 electrically isolated when device 100 is not in use. The separation channel 108 also prevents electrical shorting of electrodes within contact surfaces 104 and 106 when device 100 is in use on the skin at a therapy site. In the depicted example, separation channel 108 is a gap between first contact surface 104 and second contact surface 106. In certain embodiments, separation channel 108 may include an electrical insulator. As can be seen in FIG. 1B, in certain approaches, the device 100 includes a battery 110, which spans separation channel 108. One terminal of battery 110 is coupled to first contact surface 104, and one terminal of battery 110 is coupled to second contact surface 106 (not shown).

Figure 2:
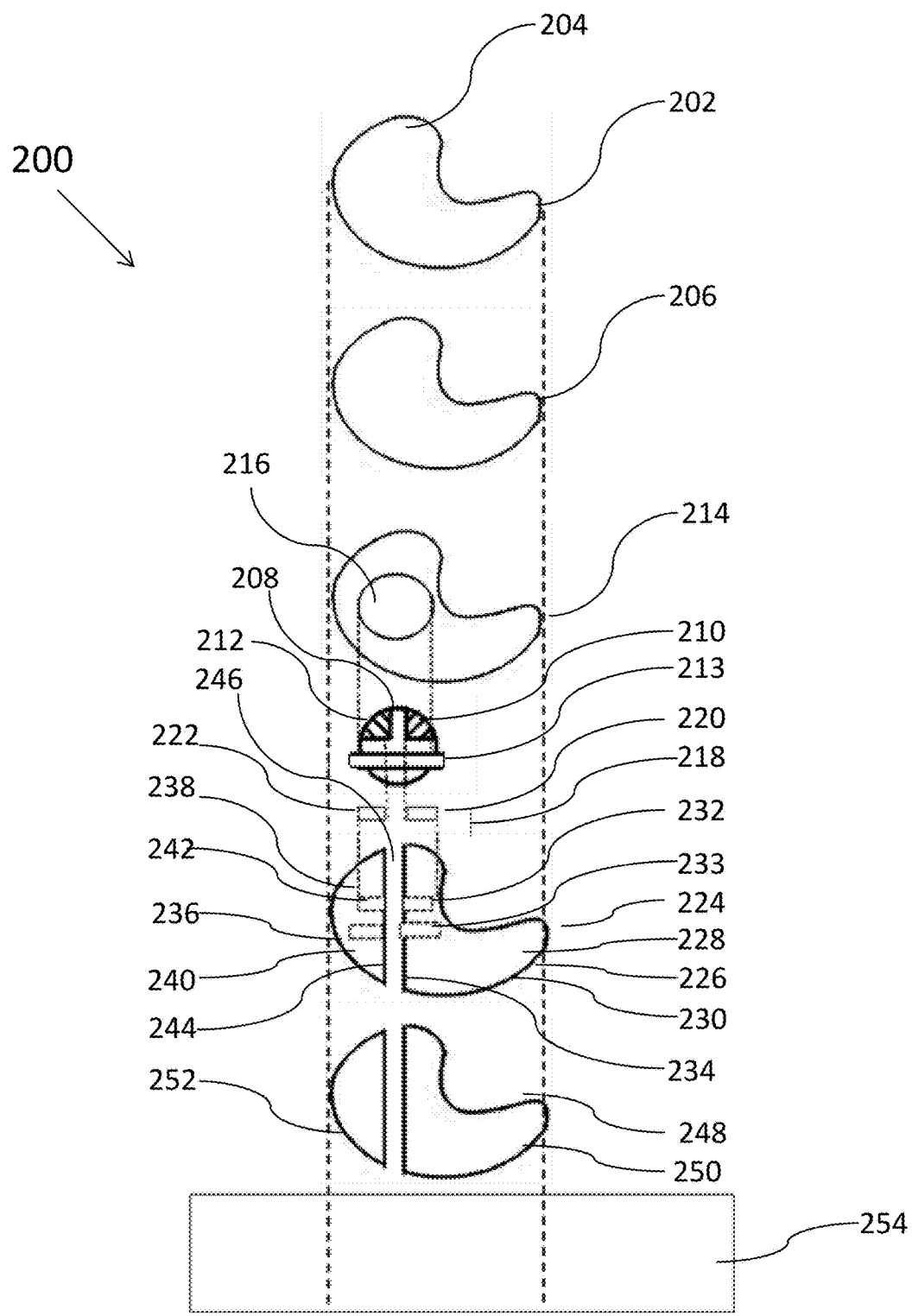
FIG. 2 depicts an exploded view of the transdermal drug delivery device of FIGS. 1A and 1B.

FIG. 2 depicts an exploded view of an embodiment of a transdermal drug delivery device. Device 200 may be similar to device 100 depicted in FIGS. 1A and 1B. In certain approaches, the device 200 is flexible to conform to a user's body. Accordingly, the individual components of the device 200 described below, may also be flexible. In certain approaches, the device 200 is also stretchable. For example, flexible, stretchable electronic components may be utilized to improve conformity, application, and adhesion to a therapy site on a user. These properties may be particularly important to enable application to virtually all users, despite anatomical differences such as the shape of the application area on the user or differences in skin texture, hydration, and oil content. The device 200 may also be shaped with specific contours for application to portions of a user's body, such as the forehead or eye region, as will be described in greater detail herein.

The device 200 includes a base layer 202. The base layer 202 includes an upper surface 204, which may be similar to upper surface 102. For example, the upper surface 204 may include texturing to improve usability when applying device 200 on the skin surface. In certain approaches, base layer 202 is flexible. For example, base layer 202 may be constructed of a material, such as a woven fabric, non-woven fabric, or polymer substrate. The base layer 202 provides the overall shape of device 200. In some embodiments, the base layer 202 may be formed from a "breathable" material, i.e., a material that is readily permeable by water vapor or liquid. In some embodiments, the base layer 202 may be formed from a material that is not readily permeable by water vapor or liquid. Examples of such materials may include a plastic medical tape and a woven plastic, for example, woven rayon. Permeability may be further limited by including multiple materials in the base layer 202. For example, the base layer 202 may include a layer of woven rayon material underlaid by a layer of vinyl backing material. By using a substantially impermeable base layer 202, more moisture may be retained between base layer 202 and the user's tissue when device 200 is in use. This additional moisture may help to maintain or increase the hydration and/or plumpness of the tissue of the therapeutic site, providing a cosmetic benefit. Increasing the hydration of the tissue of the therapeutic site may also improve the efficacy of drug delivery to the therapeutic site, in some embodiments. While retaining moisture may be problematic for therapeutic applications in which a device or bandage is to remain in contact with the user's tissue for an extended period of time, certain applications, for example, cosmetic applications, which utilize shorter treatment times may take advantage of such moisture retention to improve therapy.

As described below, the device 200 includes additional components, which are coupled directly or indirectly to the base layer 202. For example, some components may be coupled to other components, which couple directly to base layer 202 of device 200. In certain approaches, adhesives are used to couple components of device 200, or the materials of the components are adhesive.

In certain approaches, device 200 includes a spacing layer 206. The spacing layer 206 may provide cushioning to protect electronic components of device 200. In certain approaches, spacing layer 206 is a vinyl or foam layer. Additionally or alternatively, spacing layer 206 may be an electrical insulator. The spacing layer 206 may compensate for differences in the stiffness or rigidity of different components of device 200 to provide a uniform feel of device 200 and allow for uniform adhesion to a therapy site on a user. For example, battery 208 may be more rigid than base layer 202. Accordingly, spacing layer 206 may provide sufficient cushioning to absorb differences in flexibility of these components. The spacing layer 206 may also adjust the overall thickness of the device 200 to enable the application and removal of device 200 from a therapy site. For example, the device 200 should be sufficiently thick as to allow the user to grip the device 200 when removing it from packaging or from the skin. For example, the device 200 may have a thickness of between approximately 0.25 mm and approximately 7 mm, but any appropriate thickness may be used. In certain embodiments, the spacing layer 206 is coupled to base layer 202 with an adhesive. For example, the base layer 202 may include an adhesive on the side that contacts spacing layer 206. In certain approaches, the spacing layer 206 includes an adhesive. In certain approaches, the spacing layer 206 is integrally formed with the base layer 202. For example, the base layer 202 may be formed of a material, such as foam, that provides sufficient spacing, insulation, and/or rigidity compensation. In certain approaches, device 200 does not include spacing layer 206. Although spacing layer 206 is shown as having a similar shape as base layer 202, in certain approaches, spacing layer 206 may have other shapes, for example, to compensate for differences in the thickness of other layers as described below.

The device 200 includes a retention layer 214 for holding and positioning battery 208. The retention layer 214 includes a recessed region or aperture 216. The aperture 216 has a shape and size similar to that of battery 208 such that battery 208 fits within and is retained by aperture 216. In certain approaches, battery 208 is held within aperture 216 with a tight fit or a friction fit. The retention layer 214 positions battery 208 such that battery 208 is in electrical communication with first electrode 226 and second electrode 236 of electrode layer 224. In certain approaches, battery 208 has the same thickness as retention layer 214. In certain approaches, battery 208 is thinner than retention layer 214. The spacing layer 206 may be shaped similar to battery 208, and placed over battery 208 within aperture 216 to compensate for thickness differences and provide an even surface for base layer 202. Similarly, if the battery 208 is thicker than the retention layer 214, the spacing layer 206 may be shaped similarly to the retention layer 214 to compensate for the thickness differences. In certain approaches, device 200 does not include retention layer 214. For example, base layer 202 or spacing layer 206 may directly cover battery 208, or may include a recessed portion for retaining and positioning battery 208 relative to electrode layer 224. In some embodiments, retention layer 214 may not be included, but spacing layer 206 may be included. In some such embodiments, spacing layer 206 may be a plastic layer, for example, a vinyl layer, having a thickness of less than 0.5 mm, for example, 0.1 mm, and may serve to cover battery 208 and hold it in place. The spacing layer 206 may be an substantially impermeable layer, which may take the form of any of the embodiments of impermeable layers discussed above, and may confer some or all of the features and benefits discussed above.

The device 200 includes a power supply, such as battery 208. Although the power supply is depicted as battery 208, alternative power supplies may be used. For example, electrical power may be provided through an inductive power receiver. Integrating the power supply directly into device 200 allows device 200 to be a freestanding device without the need to plug-in or tether device 200 to an external power supply. In certain approaches, device 200 includes a plurality of power supplies. For example additional power supplies may be used to provide increased voltage or prolong battery life. In certain approaches, battery 208 is a thin-form battery, such as a printed battery, paper-based battery, or lithium ion battery. The battery 208 is flexible to allow device 200 to conform to a therapy site on a user. In certain approaches, battery 208 is stretchable to further improve the ability of device 200 to conform to a therapy site. In certain approaches, battery 208 is rechargeable. The battery 208 may be removable or replaceable. The battery 208 may be integrated with a circuit including additional passive or active electronics, as described below with reference to electronics layer 314. For example, in some embodiments, device 200 may be configured to supply a pulsing current.

As depicted in FIG. 2, battery 208 includes a first terminal 210 and a second terminal 212. These terminals 210 and 212 correspond to positive and negative terminals. Depending on the application and the molecule to be delivered, either terminal 210 or terminal 212 can be configured as the positive or the negative terminal. In certain approaches, device 200 includes tape 213 for adhering battery 208 to electrode layer 224, for example, at indicated position 233. Additionally or alternatively, other adhesive or retention mechanisms may be used, including, but not limited to, epoxies or other adhesives. In certain approaches, retention layer 214 covers tape 213 when battery 208 is positioned within retention layer 214 to further secure tape 213, and therefore battery 208, to electrode layer 224. In certain approaches, battery 208 is secured in device 200 without tape 213. In certain approaches, retention layer 214 contacts and covers battery 208 to secure battery 208 within device 200. In certain approaches, spacing layer 206 contacts and covers battery 208 to secure battery 208 within device 200.

In certain embodiments, the electrical connection between terminals 210 and 212 of battery 208 and the electrodes 226 and 236, respectively, is made with conductive tape 218. Additionally or alternatively, the electrical connection between terminals 210 and 212 and the electrodes 226 and 236 respectively, for example, as illustrated with conductive tape 218, may be made with conductive epoxies, bonding, for example, bump bonding or wire bonding, ultrasonic welding, adhesives, or other dispensed materials. The conductive tape 218 or other conductive material may be isotropically or anisotropically conductive. In certain approaches the electrical connection is formed by direct contact between battery 208 and electrodes 226 and 236 without tape, adhesive, or other bonds.

The conductive tape 218 has a first piece 220, which connects first terminal 210 to first electrode 226, for example, at indicated position 232. The conductive tape 218 has a second piece 222, which connects second terminal 212 to second electrode 226, for example at indicated position 242. In certain approaches, conductive tape 218 is a double-sided adhesive tape to effectively couple to both the battery 208 and the electrode layer 224.

In certain approaches, conductive tape 218 is anisotropic conductive tape, which only allows current to flow along the z-axis, i.e., up or down between the layers conductive tape 218 contacts, but does not allow the current to flow laterally. Using anisotropic conductive tape as conductive tape 218 may prevent electrical shorts between the first terminal 210 and second terminal 212 of battery 208 or between first electrode 226 and second electrode 236 of electrode layer 224. Using anisotropic conductive tape as conductive tape 218 may also simplify the construction of device 200. For example, conductive tape 218 may be a single piece of tape, spanning, including, or replacing pieces 220 and 222, which physically connects battery 208 to electrode layer 224. Since an anisotropic embodiment of conductive tape 218 only electrically conducts along the z-axis, conductive tape 218 connects first terminal 210 to first electrode 226, and second terminal 212 to second electrode 236, but does not electrically connect first terminal 210 to second terminal 212 or first electrode 226 to second electrode 236.

In certain embodiments, electrode layer 224 is constructed of a multi-layered electrode material. The first electrode 226 has an upper first conductance layer 228 and a lower first interface layer 230. Similarly, second electrode 236 has an upper second conductance layer 238 and a lower second interface layer 240. When the device 200 is in use, interface layers 230 and 240 are positioned between the user's tissue and the conductance layers 228 and 238, respectively, and thus provide an "interface" between the user and the conductance layers. In certain approaches, one or more of interface layers 230 and 240 are formed from one or more materials that are more resistant to oxidation or fouling, for example, that are relatively "inert" than the materials used in upper conductance layers 228 and 238, respectively. For example, in some embodiments, one or more of interface layers 230 and 240 are formed from carbon-based materials, while one or more of conductance layers 228 and 238 are formed from metal materials. By positioning materials that are less susceptible to oxidation between the user's tissue and the conductance layers 228 and 238, the formation of resistive oxidized patches or layers on electrodes 224 and 236 may be reduced or minimized, thereby reducing the likelihood of creating dangerous hotspots, maintaining current delivery at or close to its initial level, and extending the effective life of device 200. Having a stable electrical interface, i.e., one whose electrical properties do not change substantially during use or during the life of device 200, may also help ensure consistent and predictable drug delivery by maintaining consistent and predictable current and voltage relationships. The composition of materials used in interface layers 230 and 240 may be the same, or may be different.

In certain approaches, when relatively inert materials are used for one or more of interface layers 230 and 240, interface layers 230 and/or 240 may have higher resistivity than materials traditionally used in electrode application, for example, metal materials. However, if first electrode 226 were to only include interface layer 230 and not conductance layer 228, the resistivity of interface layer 230 may be too high for effective, even lateral distribution of current through first electrode 226. For example, if current were provided to interface layer 230 formed, for example, from carbon-impregnated vinyl, through a contact point that contacts only a small portion of interface layer 230, the current may be unevenly distributed laterally across interface layer 230, and may have the highest current density nearest the contact point. The resulting hot spot may burn the patient, while the remaining area of interface layer 230 may experience little or no current flow.

To improve the current distribution through one or more of interface layers 230 and 240 while retaining the oxidation resistant properties discussed above, in some embodiments, conductance layer 228 and/or conductance layer 238 may be formed from lower resistivity and higher conductivity materials than interface layers 230 and 240, respectively. For example, one or more of interface layers 230 and 240 may be formed from a carbon-impregnated plastic, for example, a carbon-impregnated vinyl, while conductance layer 228 and/or conductance layer 238 are formed from metal materials, for example, silver. The higher conductivity of the upper conductance layers may allow the lateral distribution of current to be achieved in those layers and then maintained in the lower conductivity interface layers. By including a stable and inert interface layer and a conductive upper layer, the multi-layered electrode materials disclosed herein may provide improved performance over traditional electrode constructions. The conductance layers 228 and 238 are electrically connected to battery 208, for example, through conductive tape 218. The conductance layers 228 and 238 completely cover interface layers 230 and 240, respectively, so that when current is provided to conductance layers 228 and 238, the current is distributed throughout the entire interface layers 230 and 240.

In certain approaches, first conductance layer 228 is integrally coupled to interface layer 230, and second conductance layer 238 is integrally coupled to interface layer 240. For example, first conductance layer 228 may be formed on interface layer 230 through printing, extrusion, vapor deposition, etching, lithography, or adhesion processes. Similarly, second conductance layer 238 may be formed on interface layer 240 through printing, extrusion, vapor deposition, or adhesion processes. In various embodiments, first interface layer 230 and second interface layer 240 may be formed of other materials including, but not limited to, silver, silver chloride, aluminum, zinc, nickel, gold, carbon and platinum. In various embodiments, first conductance layer 228 and second conductance layer 238 may be formed of other materials including, but not limited to, silver, silver chloride, aluminum, zinc, nickel, gold, carbon and platinum. In certain approaches, as discussed above, first conductance layer 228 has a higher conductivity than first interface layer 230, and conductance layer 238 has a higher conductivity than second interface layer 240. In other embodiments, first conductance layer 228 has a conductivity similar to or lower than a conductivity of first interface layer 230, and/or second conductance layer 238 has a conductivity similar to or lower than a conductivity of second interface layer 240. In some embodiments, one or more of first conductance layer 228, first interface layer 230, second conductance layer 238 and second interface layer 240 may be omitted.

The first electrode 226 and second electrode 236 of electrode layer 224 are flexible to allow device 200 to conform to a therapy site. In certain approaches, electrode layer 224 is stretchable to enable increased conformity to a therapy site. The electrode layer 224 may have a thickness of between approximately 0.05 mm and approximately 2 mm, although any appropriate thickness may be used. In some embodiments, the electrode layers disclosed herein may be substantially impermeable layers, which may take the form of any of the embodiments of impermeable layers discussed above, and may confer some or all of the features and benefits discussed above.

The first electrode 226 and second electrode 236 are physically separated and electrically isolated along first inner edge 234 and second inner edge 244 to form separation channel 246. The separation channel 246 keeps first electrode 226 and second electrode 236 electrically isolated when device 200 is not in use. The separation channel 246 also prevents electrical shorting of electrodes 226 and 236 when the device is in use on the skin at a therapy site. In the depicted example, separation channel 246 is a gap between first electrode 226 and second electrode 236. In certain embodiments, separation channel 246 may include an electrical insulator. The first electrode 226 and second electrode 236 are coupled to retention layer 214, for example, through an adhesive and are thereby coupled to base layer 202. In some embodiments, battery 208 is not positioned over separation channel 246. For example, battery 208 may be to various portions of device 200 by leads, which may be included in an electronics layer, for example, similar to electronics layer 314, discussed below, or in a separate layer.

The device 200 includes coupling layer 248, which has a first coupling surface 250 and second coupling surface 252. The first coupling surface 250 is coupled to first electrode 226 and second coupling surface 252 is coupled to second electrode 236. The coupling layer 248 may be flexible and conformal. The coupling layer 248 may also be adhesive. For example, coupling layer 248 may be a soft, flexible, conductive, adhesive gel or hydrogel. In certain approaches, coupling layer 248 is a foam, sponge, mesh, or polymer matrix. In certain approaches, device 200 is manufactured with a release liner 254, from which the user removes device 200 before applying device 200 to a therapy site.

In practice, a user places a therapeutic formulation, such as a lotion or serum, containing a therapeutic agent, on the skin at a therapy site. For example, the devices and systems described herein may be used for treating wrinkles on the face, such as on the forehead or around the eye, i.e., "crow's feet". The serum may include a therapeutic agent, for example, one or more molecules, for reducing wrinkles. In certain approaches, therapeutic agent molecules have a non-neutral charge. In use, device 200 is placed on a therapy site with coupling layer 248 directly contacting the user's skin. The entire device 200 is flexible and conforms to the therapy site. The user is able to press on upper surface 204 to position the device on the skin. The coupling layer 248 conforms and adheres to the skin to provide a stable device-skin interface for consistent current delivery. In certain approaches, coupling layer 248 hydrates the skin upon contact and reduces the skin impedance. In certain embodiments, coupling layer 248 may include therapeutic agents instead of or in addition to the separate application of a therapeutic agent to the user's skin prior to the application of device 200.

When coupling layer 248 of device 200 contacts the skin, a closed current path is formed from first terminal 210 of battery 208 through tape 218, through first conductance layer 228 and first interface layer 230 of first electrode 226, through first coupling surface 250, to the skin, through second coupling surface 252, through second interface layer 240 and second conductance layer 238 of second electrode 236, through conductive tape 218, to second terminal 212 of battery 208. Similarly, the current may flow in the opposite path from second terminal 212 to first terminal 210 of battery 208 depending on the polarity of the terminals. The flow of current drives the therapeutic agent into the skin at the therapy site. In certain approaches, such as cosmetic applications, the agent may be delivered only into the upper layers of the skin, but not delivered systemically.

Figure 3:
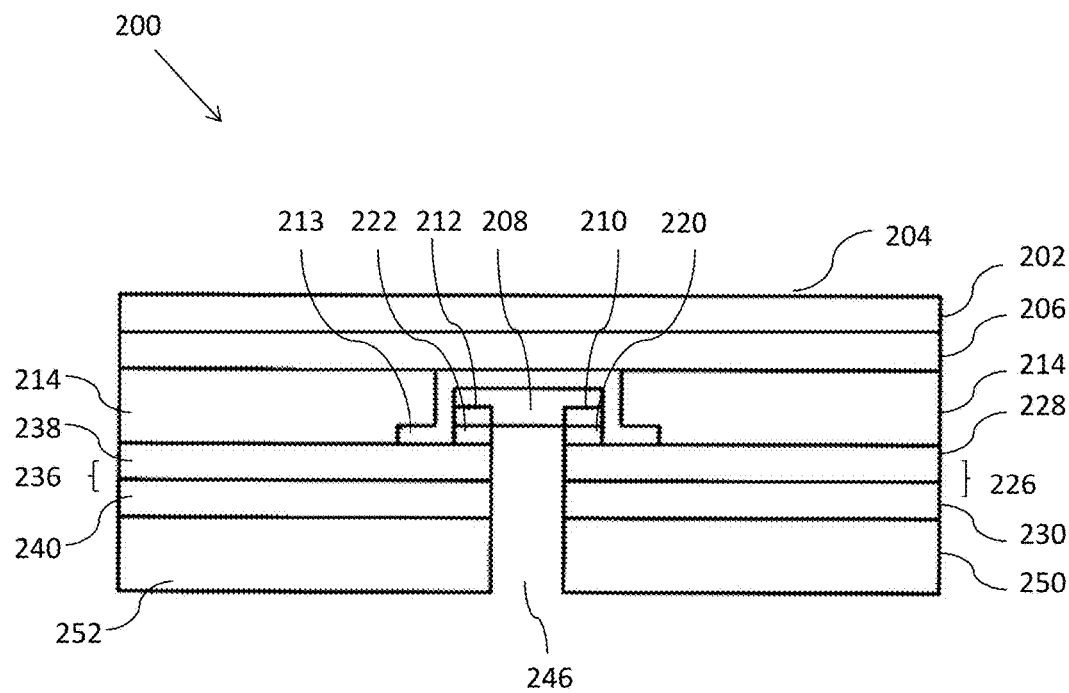
FIG. 3 illustrates a cross-sectional side view of the transdermal drug delivery device of FIG. 2.

FIG. 3 illustrates a cross-sectional side view of transdermal drug delivery device 200 of FIG. 2. The layers depicted in FIG. 3 are illustrated for clarity, but are not necessarily drawn to scale. As previously described in relation to FIG. 2, device 200 includes base layer 202 with upper surface 204, spacing layer 206, retention layer 214, first electrode 226, second electrode 236, first coupling surface 250, second coupling surface 252, battery 208, tape 213, first conductive tape piece 220, and second conductive tape piece 222. Battery 208 spans channel 246, which separates first electrode 226 and first coupling surface 250 from second electrode 236 and second coupling surface 252. In certain approaches, battery 208 is positioned in place and secured by tape 213, which goes over battery 208 and between retention layer 214 and electrodes 228 and 238. Battery 208 may also be further secured by conductive tape pieces 220 and 222.

First terminal 210 of battery 208 is electrically connected to first conductance layer 228 of first electrode 226 by first tape piece 220. As discussed above, in some embodiments, the high conductivity of first conductance layer 228 allows the current to be substantially evenly distributed through first interface layer 230, which has a lower conductivity than first conductance layer 228. Similarly, second terminal 212 of battery 208 is electrically connected to second conductance layer 238 of second electrode 236 by second tape piece 222. In some embodiments, the high conductivity of second conductance layer 238 allows the current to be substantially evenly distributed through second interface layer 240, which has a lower conductivity than second conductance layer 238.

Figure 4:
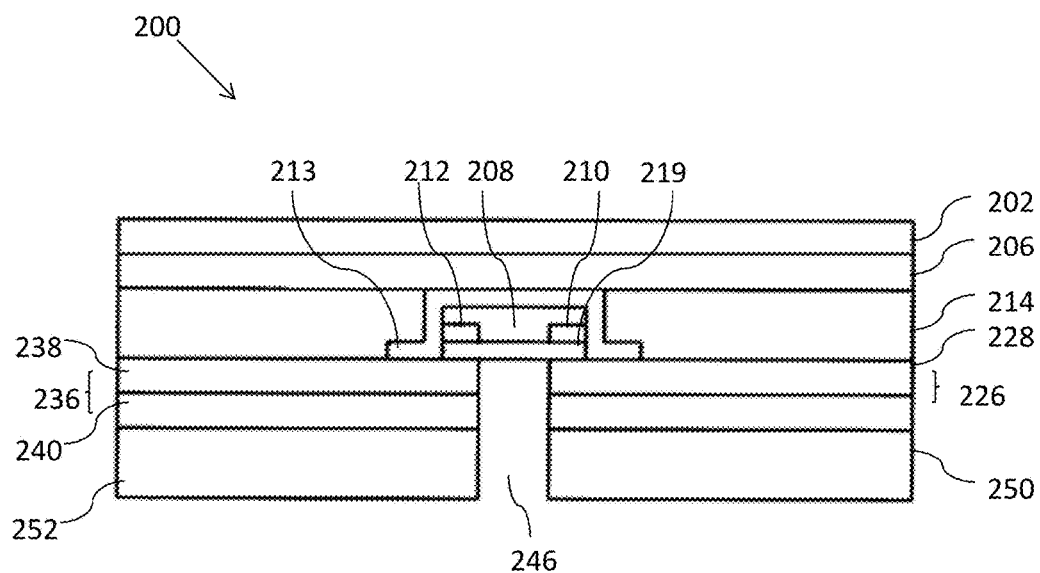
FIG. 4 depicts a cross-sectional side view of an embodiment of a transdermal drug delivery device.

In certain embodiments, as depicted in FIG. 4, conductive tape 219 spans channel 246. For example, conductive tape 219 may be anisotropic conductive tape which allows current to flow along the z-axis between first terminal 210 and first conductive layer 228, as well as between second terminal 212 and second conductive layer 238, but not directly between first terminal 210 and second terminal 212 or between first conductive layer 228 and second conductive layer 238.

Figure 5:
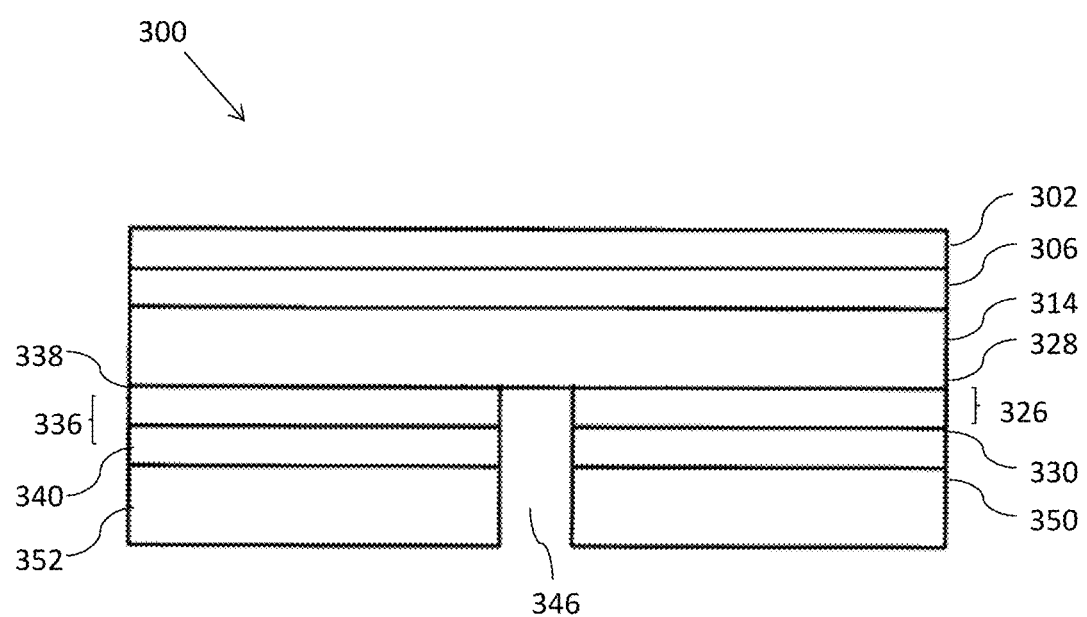
FIG. 5 depicts a cross-sectional side view of an embodiment of a transdermal drug delivery device with an integrated electronics layer.

In certain approaches, the devices, systems, and methods described herein may include integrated electronics. For example, FIG. 5 illustrates a cross-sectional side view of transdermal drug delivery device 300. Device 300 functions similarly to previously described devices 100 and 200, but includes an electronics layer 314. Device 300 includes a base layer 302 with an upper surface 304, spacing layer 306, first electrode 326 with a first conductance layer 328 and a first interface layer 330, second electrode 336 with a second conductance layer 338 and a second interface layer 340, first coupling surface 350, second coupling surface 352, and separation channel 346. Electronics layer 314 includes a power source, such as a battery or inductive power receiver. Electronics layer 314 may also include additional electronic components, such as a charge pump, microcontroller, integrated circuit, for example, operational amplifiers, timers, etc., application-specific integrated circuit (ASIC), visual indicator, for example, an LED and/or a display, audio indicator, for example, a buzzer and/or a speaker, tactile actuators for example, a vibration motor, antenna, data port, buttons or knobs, analog components, digital components, or other electronic components. In certain approaches, electronics layer 314 is or includes a printed, flexible circuit. For example, electronics layer 314 may be a printed, flexible circuit on a polyester substrate.

In certain embodiments, electronics layer 314 includes a charge pump or other circuitry to increase the applied potential between first electrode 326 and second electrode 336. For example, a 1.5 V or 3 V power supply may be used in conjunction with a charge pump to provide a large potential or a positive and negative voltage while device 300 is in use at a therapy site. In certain approaches, electronics layer 314 includes a processing device, such as a microcontroller, configured to deliver a current with specified delivery parameters. Example of parameter includes but is not limited to at least one of time, duration, frequency and amplitude. In certain approaches, the microcontroller is programmable, for example, through a connection with a data port or through input received via an antenna, for example, BLUETOOTH). For example, device 300 may be programmable from a computer or a phone. In certain approaches, device 300 may include indicators, such as a green LED to indicate successful operation of device 300 and a red LED to indicate unsuccessful operation of device 300. For example, device 300 may measure the current output or impedance between electrodes 326 and 336 to determine whether the device has been appropriately placed at the therapy site.

In certain approaches, the parameters of the current delivered may be adjustable by a user, for example, through buttons, knobs, or other adjustment mechanisms. Since different people may be more or less sensitive to electrical current, adjusting the current automatically or manually may allow for improved comfort during drug delivery. In certain approaches, device 300 may include a processing device configured to switch the direction of current flow during delivery. In certain approaches, switching the direction of current flow may prevent passive delivery of molecules through the skin. Additionally or alternatively, a first therapeutic agent may be delivered with at a first current parameter set, and second therapeutic agent may be delivered with a second current parameter set, for example, reversed current direction.

Figure 6:
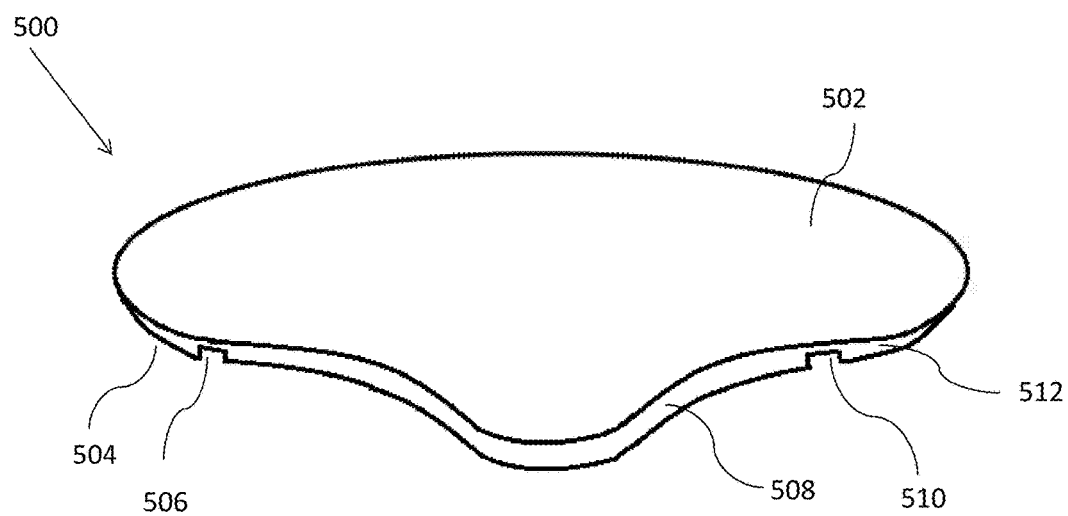
FIG. 6A depicts a top perspective view of an embodiment of a transdermal drug delivery device configured for transdermal drug delivery to the forehead.
FIG. 6B depicts a bottom perspective view of an embodiment of a transdermal drug delivery device configured for transdermal drug delivery to the forehead.
Figure 6:
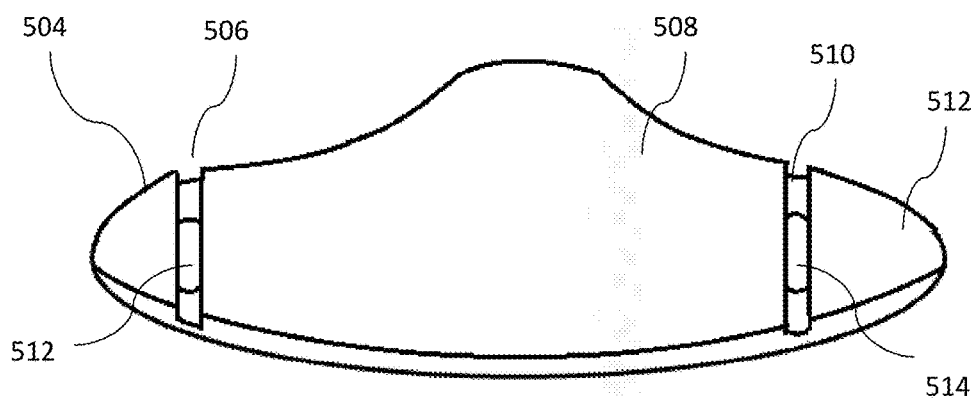

Devices 100, 200, and 300 have been depicted with two electrodes, for example, first electrode 228 and second electrode 238. In certain approaches, the devices, systems, and methods described herein may include more than two electrodes. For example, FIGS. 6A and 6B depict a transdermal drug delivery device 500 with three contact surfaces configured for transdermal drug delivery on the forehead. In particular, FIG. 6A depicts a top perspective view of device 500 and FIG. 6B depicts a bottom perspective view of device 500. Device 500 is placed on the skin for delivering a therapeutic agent, for example, therapeutic molecules to a therapy site, such as treating wrinkles on the forehead.

Device 500 includes an upper surface 502. In certain approaches, upper surface 502 may include texturing to improve a user's ability to apply device 500 to a portion of the body. For example, the texturing may provide friction, which allows the user to effectively press and apply device 1500 on a therapy site. Device 500 includes a first contact surface 504, a second contact surface 508, and a third contact surface 512, which are placed on the skin when device 500 is in use. First contact surface 504, second contact surface 508, and third contact surface 512, may include electrodes, gels, and other components for drug delivery as described in further detail herein. The first contact surface 504 and the second contact surface 508 are spaced apart by separation channel 506. Similarly, second contact surface 508 and third contact surface 512 are spaced apart by separation channel 510. Separation channels 506 and 510 keep first contact surface 504, second contact surface 508, and third contact surface 512 electrically isolated when device 500 is not in use. Separation channels 506 and 510 also prevent electrical shorting of electrodes within contact surfaces 504, 508, and 512 when device 500 is in use on the skin at a therapy site. In the depicted example, separation channels 506 and 510 are gaps between first contact surface 504, second contact surface 508 and third contact surface 512. In certain embodiments, separation channels 506 and 510 may include an electrical insulator. As can be seen in FIG. 5B, in certain approaches, device 500 includes batteries 512 and 514, which span separation channels 506 and 510, respectively. As discussed above with reference to FIG. 1, the terminals of batteries 512 and 514 may be coupled to corresponding contact surfaces.

Figure 7:
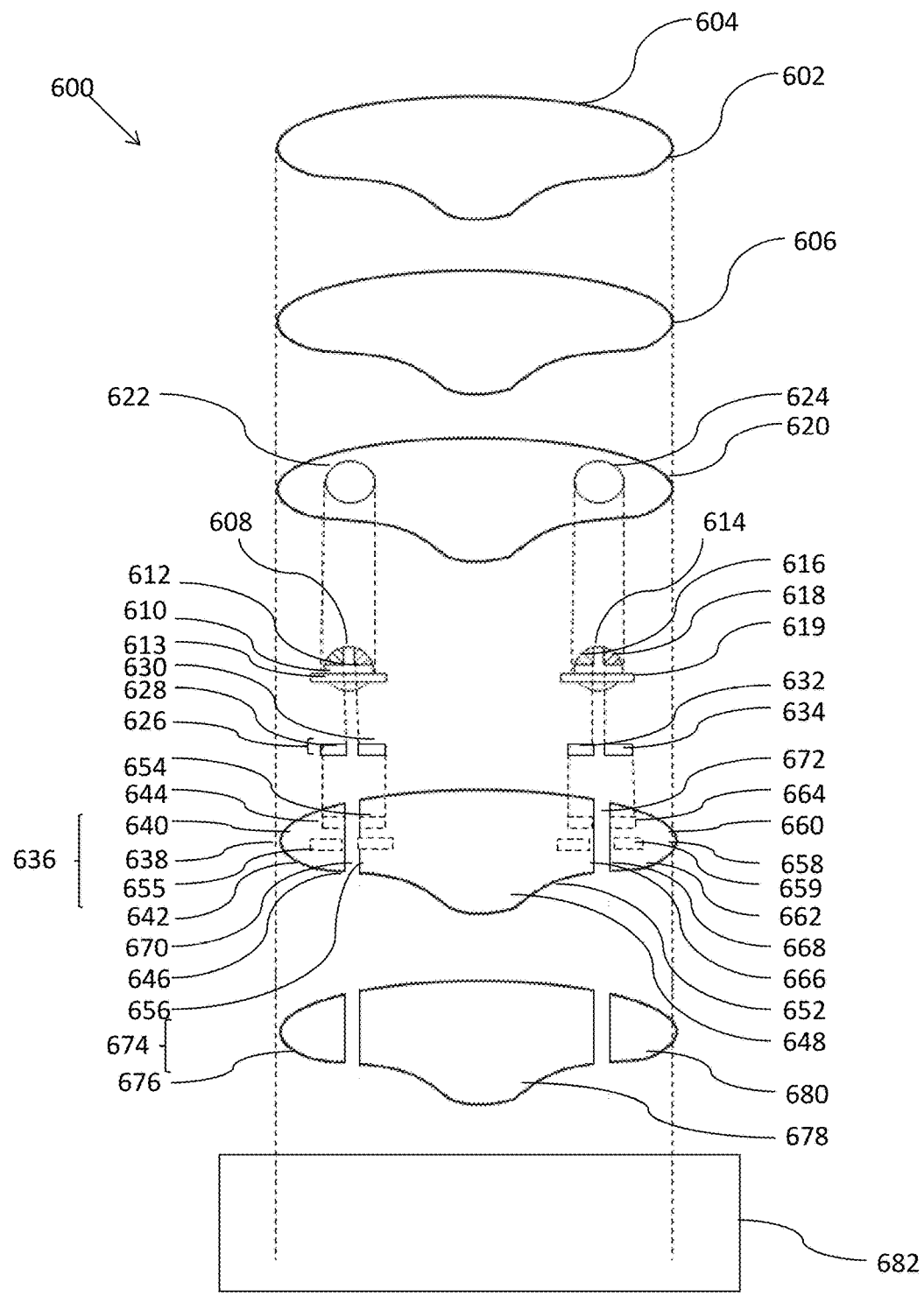
FIG. 7 depicts an exploded view of an embodiment of a transdermal drug delivery device configured for transdermal drug delivery to the forehead.

FIG. 7 depicts an exploded view of an embodiment of a transdermal drug delivery device. Device 600 may be similar to device 500 depicted in FIGS. 6A and 6B. In certain approaches, device 600 is flexible to conform to a user's body. Accordingly, the individual components of device 600 described below, may also be flexible. In certain approaches, device 600 is also stretchable. For example, flexible, stretchable electronic components may be utilized to improve conformity, application, and adhesion to a therapy site on a user. These properties may be particularly important to enable application to virtually all users, despite anatomical differences such as shape of the application area on the user or differences in skin texture, hydration, and oil content. Device 600 may also be shaped with specific contours for application to portions of a user's body, such as the forehead or eye region, as will be described in greater detail herein.

Device 600 includes base layer 602. Base layer 602 includes an upper surface 604, which may be similar to upper surface 502. For example, upper surface 604 may include texturing to improve usability when applying device 600 on the skin surface. In certain approaches, base layer 602 is flexible. For example, base layer 202 may be constructed of a material, such as a woven fabric, non-woven fabric, or polymer substrate. Base layer 602 provides the overall shape of device 600. As described below, device 600 includes additional components, which are coupled directly or indirectly to base layer 602. For example, some components may be coupled to other components which couple directly to base layer 602 of device 600. In certain approaches, adhesives are used to couple components of device 600, or the materials of the components are adhesive. As discussed above with reference to FIG. 2, base layer 602 may be formed from a breathable material or from a material that is not readily permeable by water vapor or liquid. Use of the latter materials may advantageously retain additional moisture in the user's tissue.

In certain approaches, device 600 includes a spacing layer 606. Spacing layer 606 may provide cushioning to protect electronic components of device 600. In certain approaches, spacing layer 606 is a vinyl or foam layer. Additionally or alternatively, spacing layer 606 may be an electrical insulator. Spacing layer 606 may compensate for differences in the stiffness or rigidity of different components of device 600 to provide a uniform feel of device 600 and allow for uniform adhesion to a therapy site on a user. For example, batteries 608 and 614 may be more rigid than base layer 602. Accordingly, spacing layer 606 may provide sufficient cushioning to absorb differences in flexibility of these components. Spacing layer 606 may also adjust the overall thickness of device 600 to enable the application and removal of device 600 from a therapy site. For example, device 600 should be sufficiently thick as to allow the user to grip device 600 when removing it from packaging or from the skin. For example, device 600 may have a thickness of between approximately 0.25 mm and approximately 7 mm, but any appropriate thickness may be used. For example, in some embodiments, spacing layer 606 may be a vinyl layer with a thickness of approximately 0.1 mm. In certain embodiments, spacing layer 606 is coupled to base layer 602 with an adhesive. In certain approaches, spacing layer 606 is integrally formed with base layer 602. For example, base layer 602 may be formed of a material, such as foam, that provides sufficient spacing, insulation, and/or rigidity compensation. In certain approaches, device 600 does not include spacing layer 606. Although spacing layer 606 is shown as having a similar shape as base layer 602, in certain approaches, spacing layer 606 may have other shapes, for example, to compensate for differences in the thickness of other layers as described below. Spacing layer 606 may be an substantially impermeable layer, which may take the form of any of the embodiments of impermeable layers discussed above, and may confer some or all of the features and benefits discussed above.

Device 600 includes a retention layer 620 for holding and positioning batteries 608 and 614. Retention layer 614 includes recessed regions or apertures 622 and 624. Apertures 622 and 624 are sized and shaped similar to that of batteries 608 and 614, such that batteries 608 and 614 fit within and are retained by aperture apertures 622 and 624. Retention layer 620 positions batteries 608 and 614 such that batteries 608 and 614 are in electrical communication with first electrode 638, second electrode 648, and third electrode 658 of electrode layer 636. In certain approaches, batteries 608 and 614 have the same thickness as retention layer 620. In certain approaches, batteries 608 and 614 are thinner than retention layer 620. Spacing layer 606 may be shaped similarly to batteries 608 and 614, and placed over batteries 608 and 614 within apertures 622 and 624 to compensate for the thickness differences and provide an even surface for base layer 602. Similarly, if batteries 608 and 614 are thicker than retention layer 620, spacing layer 606 may be shaped similar to retention layer 620 to compensate for thickness differences. In certain approaches, device 600 does not include retention layer 620. For example, base layer 602 or spacing layer 606 may directly cover batteries 608 and 614, or may include a recessed portion for retaining and positioning batteries 608 and 614 relative to electrode layer 636.

Device 600 includes one or more power supplies, such as batteries 608 and 614. Although the power supply is depicted as batteries 608 and 614, alternative power supplies may be used. For example, electrical power may be provided through an inductive power receiver. Integrating the power supply directly into device 600 allows device 600 to be a freestanding device without the need to plug-in or tether device 600 to an external power supply. Additional power supplies may be used to provide increased voltage or prolong battery life. In certain approaches, batteries 608 and 614 are thin-form batteries, such as a printed batteries, paper-based batteries, or lithium ion batteries. Batteries 608 and 614 may be flexible to allow device 600 to conform to a therapy site on a user. In certain approaches, batteries 608 and 614 are stretchable to further improve the ability of device 600 to conform to a therapy site. In certain approaches, batteries 608 and 614 are rechargeable. Batteries 608 and 614 may be removable or replaceable. Although two batteries 608 and 614 are depicted, any appropriate number of power supplies. In certain approaches, device 600 includes one battery, wherein one electrode or set of electrodes are in electrical communication with a first terminal and a second electrode or set of electrodes are in electrical communication with a second terminal.

As depicted in FIG. 7, battery 608 includes a first terminal 610 and a second terminal 612. Battery 612 includes a third terminal 616 and fourth terminal 618. These terminals 610, 612, 616, and 618 correspond to positive and negative terminals. The arrangement of the battery terminals is dependent on the application and the molecule to be delivered. For example, the negative terminals of both batteries 612 and 618 may be configured to contact second electrode 648. Alternatively, device 600 may be configured such that a second electrode 648 is coupled to a positive terminal from a one battery and a negative terminal from a second battery. This latter configuration may be used to provide currents in different directions or of different magnitudes.

In certain approaches, device 600 includes tape 613 for adhering battery 608 to electrode layer 636, for example, at location 655, and tape 619 for adhering battery 614 to electrode layer 636, for example, at location 659. Additionally or alternatively, other adhesive or retention mechanisms may be used, including, but not limited epoxies or adhesives. In certain approaches, retention layer 620 covers tape 613 and tape 619 when batteries 608 and 614 are positioned within retention layer 620 to further secure tape 613 and tape 619, and therefore batteries 608 and 614, to electrode layer 636. In certain approaches, batteries 608 and 614 are secured in device 600 without tape 613 and 619.

In certain embodiments, the electrical connection between batteries 608 and 614 and electrodes 638, 648, and 658 is made with conductive tape 626. Additionally or alternatively, these electrical connections may be made with conductive epoxies, bonding, for example, bump bonding or wire bonding, ultrasonic bonding, adhesives, or other dispensed materials. Conductive tape 626 or other conductive material may be isotropically or anisotropically conductive. In certain approaches the electrical connection is formed by direct contact between batteries 608 and 614 and electrodes 638, 648, and 658 without tape, adhesive, or other bonds.

Conductive tape 626 has a first piece 628, which connects terminal 610 to first electrode 638 at indicated position 644. Conductive tape 626 has a second piece 630, which connects terminal 612 to second electrode 648 at indicated position 630. Conductive tape 626 has a third piece 632, which connects terminal 616 to second electrode 648 at indicated position 662. Conductive tape 626 has a fourth piece 634, which connects terminal 618 to third electrode 658 at indicated position 664. In certain approaches, conductive tape 626 is a double-sided adhesive tape to effectively couple to both battery 208 and electrode layer 224.

In certain approaches, conductive tape 626 is anisotropic conductive tape, which only allows current to flow along the z-axis, i.e., up or down between the layers conductive tape 626 contacts but does not allow the current to flow laterally. For example, conductive tape 626 may be a single piece of tape which physically connects battery batteries 608 and 614 to electrode layer 636. In certain approaches, conductive tape 626 includes a first piece of tap spanning channel 670 and a second piece of tape spanning channel 668.

In certain embodiments, electrode layer 636 is constructed of a multi-layered electrode material. Multi-layered embodiments of electrode layer 636 may take the form of any of the multi-layered embodiments discussed above with reference to FIG. 3. First electrode 638 has an upper first conductance layer 640 and a lower first interface layer 642. Similarly, second electrode 638 has an upper second conductance layer 650 and a lower second interface layer 650.

Third electrode 658 has an upper third conductance layer 660 and a lower third interface layer 662. As discussed previously in relation to interface layers 230 and 240, interface layers 642, 652, and 662 may provide a stable, inert electrode interface for delivering current. In certain approaches, interface layers 640, 650, and 660 have high resistivity. For example, interface layers 640, 650, and 660 may be formed from carbon-impregnated vinyl. As discussed previously in relation to conductance layers 228 and 238, conductance layers 640, 650, and 660 may be formed of highly conductive material, for example, high conductivity and low resistivity, such as silver. Conductance layers 640, 650, and 660 are electrically connected to batteries 608 and 614, for example, through conductive tape 626. Conductance layers 640, 650, and 660 completely cover interface layers 642, 652, and 662, respectively, so that when current is provided to conductance layers 640, 650, and 660, the current is distributed throughout the entire interface layers 642, 652, and 662.

In certain approaches, conductance layers 640, 650, and 660 are each integrally coupled to interface layers 642, 652, and 662, respectively. For example, conductance layers 640, 650, and 660 may be formed on interface layers 642, 652, and 662 through printing, extrusion, vapor deposition, etching, lithography, or adhesion processes. In various embodiments, interface layers 642, 652, and 662 may be formed of other materials including, but not limited to, silver, silver chloride, carbon, aluminum, zinc, nickel, gold, and platinum. In various embodiments, conductance layers 640, 650, and 660 may be formed of other materials including, but not limited to, silver, silver chloride, carbon, aluminum, zinc, nickel, gold, and platinum. In certain approaches, as discussed above, conductance layers 640, 650, and 660 each have a high conductivity than interface layers 642, 652, and 662, respectively. In some embodiments, one or more of conductance layers 640, 650, and 660 may have a lower conductivity than one or more of interface layers 642, 652, and 662, respectively.

First electrode 638, second electrode 648, and third electrode 658 of electrode layer 636 are flexible to allow device 600 to conform to a therapy site. In certain approaches, electrode layer 636 is stretchable to enable increased conformity to a therapy site. In certain embodiments, electrode layer 636 has a thickness of between approximately 0.05 mm and approximately 2 mm, although any appropriate thickness may be used.

First electrode 638 and second electrode 648 are physically separated and electrically isolated along first inner edge 646 and second inner edge 656 to form separation channel 670. Second electrode 648 and third electrode 658 are physically separated and electrically isolated along third inner edge 666 and fourth inner edge 668 to form separation channel 672. Separation channels 670 and 670 keep electrodes 638, 648, and 658 electrically isolated. In the depicted example, separation channels 670 and 670 are gaps between electrodes 638, 648, and 658. In certain embodiments, channels 670 and 670 may include an electrical insulator. Electrodes 638, 648, and 658 are coupled to retention layer 620, for example, through an adhesive. Electrodes 638, 648, and 658 are thereby coupled to base layer 202. Electrodes 638, 648 and 658 may include a substantially impermeable material, which may take the form of any of the embodiments of impermeable layers discussed above, and may confer some or all of the features and benefits discussed above.

Device 600 includes coupling layer 674, which has a first coupling surface 676, second coupling surface 678, and third coupling surface 680. First coupling surface 676 is coupled to first electrode 638, second coupling surface 678 is coupled to second electrode 648, and third coupling surface 680 is coupled to third electrode 658. Coupling layer 678 may be flexible and conformal. Coupling layer 674 may also be adhesive. For example, coupling layer 674 may be a soft, flexible, adhesive gel or hydrogel. In certain approaches, coupling layer 674 is a foam, sponge, mesh, or polymer matrix. In certain approaches, device 600 is manufactured with a release liner 682, from which the user removes device 600 before applying device 600 to a therapy site.

As described above, a user may place a therapeutic formulation, such as a lotion or serum, containing a therapeutic agent, on the skin at a therapy site. In practice, device 600 is placed on a therapy site with coupling layer 674 directly contacting the user's skin. The entire device 600 is flexible and conforms to the therapy site. The user is able to press on upper surface 604 to position the device on the skin. Coupling layer 674 conforms and adheres to the skin to provide a stable device-skin interface for consistent current delivery. In certain approaches, coupling layer 674 hydrates the skin upon contact and reduces the skin impedance. In certain embodiments, coupling layer 674 may include therapeutic agents instead of or in addition to the separate application of a therapeutic agent to the user's skin prior to the application of device 600.

When coupling layer 674 of device 600 contacts the skin, a closed current path is formed from first terminal 610 of battery 608 through tape 612, through first conductance layer 640 and first interface layer 642 of first electrode 638, through first coupling surface 676, to the skin, through second coupling surface 678, through second interface layer 652 and second conductance layer 650 of second electrode 648, through conductive tape 626, to second terminal 612 of battery 608. The current may flow in the opposite path from second terminal 612 to first terminal 610 of battery 608 depending on the polarity of the terminals. Similarly, a current path is formed from fourth terminal 618 of battery 614 through tape 626, through third conductance layer 660 and third interface layer 652 of third electrode 648, through third coupling surface 680, to the skin, through second coupling surface 678, through second interface layer 652 and second conductance layer 650 of second electrode 648, through conductive tape 626, to third terminal 616 of battery 614. The current may flow in the opposite path from third terminal 614 to first terminal 618 of battery 614 depending on the polarity of the terminals. In certain approaches, batteries 608 and 614 are arranged such that first terminal 610 and fourth terminal 618 have the same polarity. In certain approaches, batteries 608 and 614 are arranged such that first terminal 610 and fourth terminal 618 have the opposite polarity.

Figure 8:
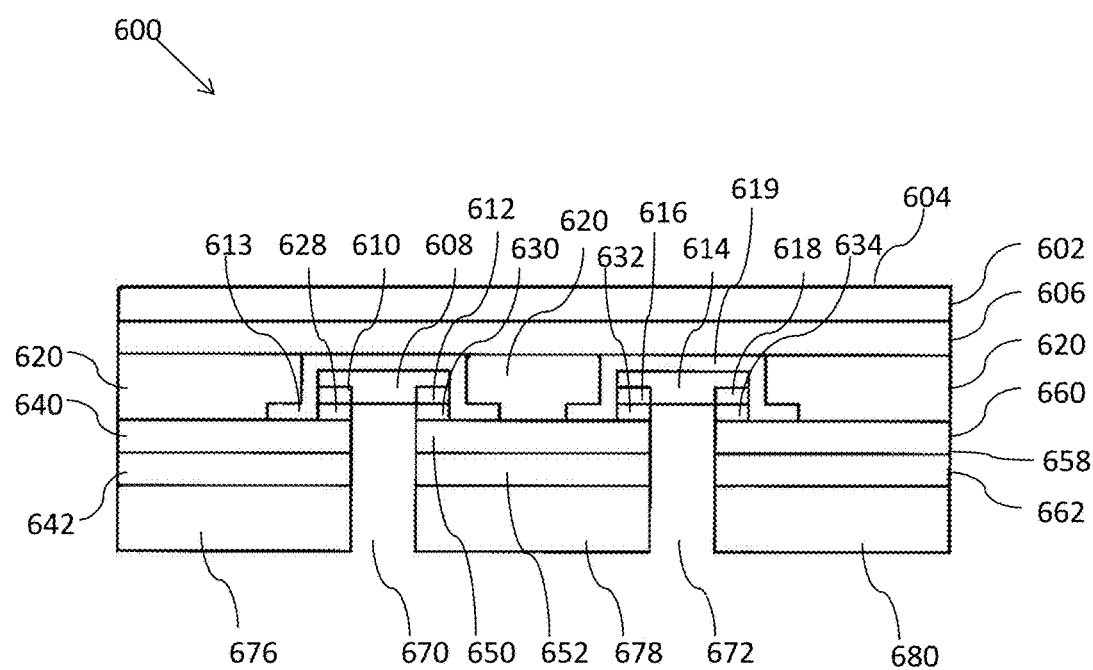
FIG. 8 depicts a cross-sectional side view of an embodiment of a transdermal drug delivery device.

FIG. 8 illustrates a cross-sectional side view of transdermal drug delivery device 600. The layers depicted in FIG. 8 are illustrated for clarity, but not necessarily to scale. As previously described in relation to FIG. 7, device 600 includes base layer 602 with an upper surface 604, spacing layer 606, retention layer 620, first electrode 638, second electrode 648, third electrode 658, first coupling surface 676, second coupling surface 678, third coupling surface 680, batteries 608 and 614, tape 613 and 619, first conductive tape piece 628, second conductive tape piece 630, third conductive tape piece 632, and fourth conductive tape piece 634. Battery 608 spans channel 670, which separates first electrode 638 and first coupling surface 676 from second electrode 648 and second coupling surface 676. In certain approaches, battery 608 is positioned in place and secured by tape 613, which goes over battery 608 and between retention layer 620 and electrodes 638 and 648. Battery 608 may also be further secured by conductive tape pieces 628 and 630. Battery 614 spans channel 672, which separates second electrode 648 and second coupling surface 678 from third electrode 658 and third coupling surface 680. In certain approaches, battery 614 is positioned in place and secured by tape 619, which goes over battery 614 and between retention layer 620 and electrodes 648 and 658. Battery 614 may also be further secured by conductive tape pieces 632 and 634. First terminal 610 of battery 608 is electrically connected to first conductance layer 640 of first electrode 638 by first tape piece 628. The high conductivity of first conductance layer 640 allows the current to be substantially evenly distributed through first interface layer 642, which has a lower conductivity than first conductance layer 642. Similarly, second terminal 612 of battery 608 is electrically connected to second conductance layer 650 of second electrode 648 by second tape piece 630, third terminal 632 of battery 614 is electrically connected to second conductance layer 650 of second electrode 648 by second tape piece 630, and fourth terminal 618 of battery 614 is electrically connected to third conductance layer 660 of third electrode 658 by fourth tape piece 634. Although not depicted, in certain approaches a single piece of anisotropic conductive tape may span either or both channels 670 and 672, as described in relation to conductive tape 219 of FIG. 4.

In certain approaches, device 600 and the other devices, systems, and methods described herein, may include an electronics layer similar to previously described electronics layer 314 of FIG. 5, or other additional electronics. For example, device 600 may include a charge pump to provide a larger applied potential between electrodes 638, 648, and 658. In certain approaches, device 600 includes a processing device, such as a microcontroller, configured to deliver a current with specified delivery parameters such as time, duration, frequency and amplitude.

Although, devices 100, 200, 300, 500, and 600 have been described with two electrodes or three electrodes, any appropriate number of electrodes may be used. For example, additional electrodes may be used to treat a large therapy area or to provide different levels of current to different portions of a therapy site.

Figure 9:
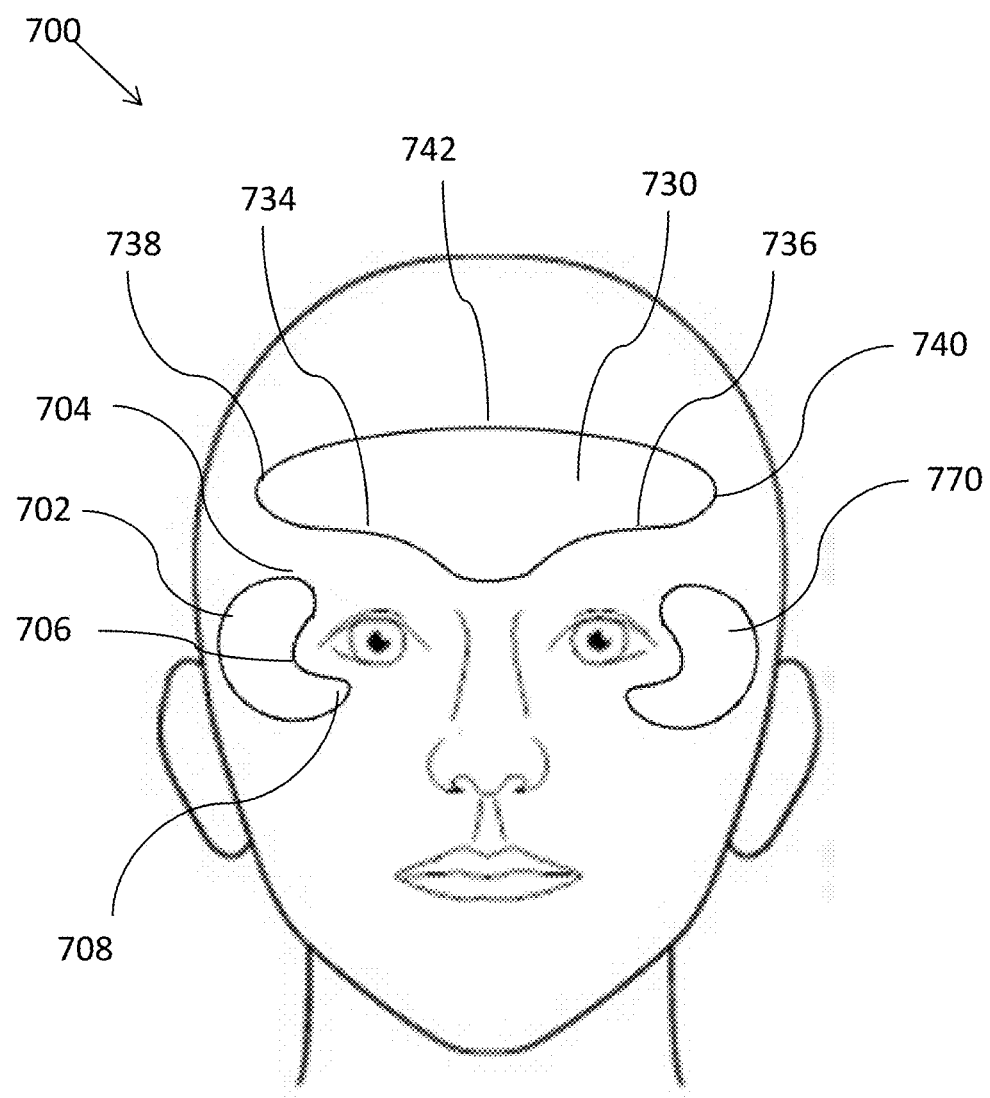
FIG. 9 depicts several transdermal drug delivery systems, configured for application to the face, applied to the face of a user.

FIG. 9 depicts an arrangement of several transdermal drug delivery devices, configured for application to the face, applied to the face of a user. Arrangement 700 includes devices 702 and 770 for treating areas near and around the eyes and side of face, for example, to treat "crow's feet" wrinkles. Arrangement 700 may also include device 730 for treating the forehead region. Although three devices 702, 730, and 770 are depicted, these devices do not necessarily need to be used simultaneously. Additionally, other devices may be configured for use on other therapy sites, including those on the face, such as the cheeks, upper lip, and chin, as well as other parts of the body.

Devices 702 and 770 are configured for treatment around the eye region. Devices 702 and 770 are flexible and adhesive to allow the devices to be placed on and conform to the therapy site. Additionally, devices 702 and 770 are shaped to effectively couple to the therapy site, and avoid irritation and discomfort. For example, device 702 includes a contour 706, which approximates the lateral shape of the orbit. Device 702 includes upper apex 704, which extends along the side of the face, around the corner and upper portion of the eye orbit. Lower apex 708 extends along the upper cheekbone and under the eye. The flexibility and contours of device 702 allow the device to be applied for simultaneously treating the side of the face near the corner of the eye, as well as under the eye.

Device 730 is configured for treatment on the forehead region. Similar to devices 702 and 770, device 730 is flexible and adhesive to allow device 730 to be placed on and conform to the therapy site. Device 730 is shaped with contours to enable effective, comfortable coupling to the therapy site. Device 730 includes contoured portions 734 and 736, which are shaped to approximate the shape of the upper orbit of the eye. For example, contours 734 and 736 may be shaped to avoid the eyebrows. Edge 742 of device 730 extends along the upper forehead region. Device 730 additionally includes apex 732. Apex 732 extends, at least partially, between the eyebrows and toward the bridge of the nose. This facial region is often an area with wrinkles, and apex 732 allows this region to be treated simultaneously with the forehead. Rounded edges 738 and 740 extend laterally along the forehead, and in certain approaches, over the side of the head toward or over the temples. These edges 738 and 740 provide effective coupling to the therapy site, with sufficient coverage over the forehead region.

Various aspects of the transdermal drug delivery devices discussed above may be modified, adjusted, and combined in a number of ways. For example, a first class of transdermal drug delivery devices may be constructed largely as described above with reference to device 200 of FIG. 2, but may omit spacing layer 206 and retention layer 214. In embodiments of this first class of devices, base layer 202 may be formed from parallel layers of woven rayon and an adhesive vinyl backing. In embodiments of this first class of devices, electrode layer 224 may have a multi-layered structure with a higher conductivity conductance layer and a lower conductivity interface layer (for example, as described above with reference to FIG. 3). The conductance layer may be a printed silver layer, and the interface layer may be a carbon-impregnated nylon layer. In embodiments of this first class of devices, tape pieces 220 and 222 may be isotropic. In embodiments of this first class of devices, coupling layer 248 may be a hydrogel layer, which may or may not be impregnated with a therapeutic agent. All additional variations and embodiments discussed above with reference to device 200 may provide variations and embodiments of the first class of devices.

A second class of transdermal drug delivery devices may be constructed largely as described above with reference to device 600 of FIG. 7, but may omit spacing layer 606 and retention layer 620. In embodiments of this second class of devices, base layer 602 may be formed from parallel layers of woven rayon and an adhesive vinyl backing. In embodiments of this second class of devices, electrode layer 636 may have a multi-layered structure with a higher conductivity conductance layer and a lower conductivity interface layer (for example, as described above with reference to FIG. 8). The conductance layer may be a printed silver layer, and the interface layer may be a carbon-impregnated nylon layer. In embodiments of this second class of devices, tape pieces 628, 630, 632 and 634 may be isotropic. In embodiments of this second class of devices, coupling layer 674 may be a hydrogel layer, which may or may not be impregnated with a therapeutic agent. All additional variations and embodiments discussed above with reference to device 600 may provide variations and embodiments of the second class of devices.

Figure 10:
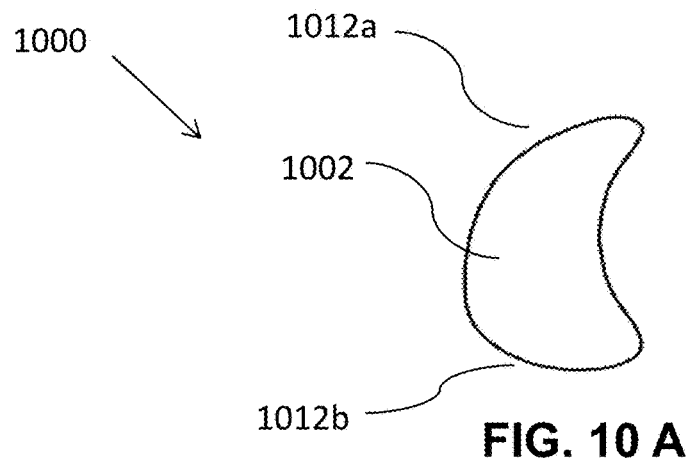
FIG. 10A depicts a top perspective view of an embodiment of a transdermal drug delivery device.
FIG. 10B depicts a bottom perspective view of the transdermal drug delivery device of FIG. 10A.
Figure 10:
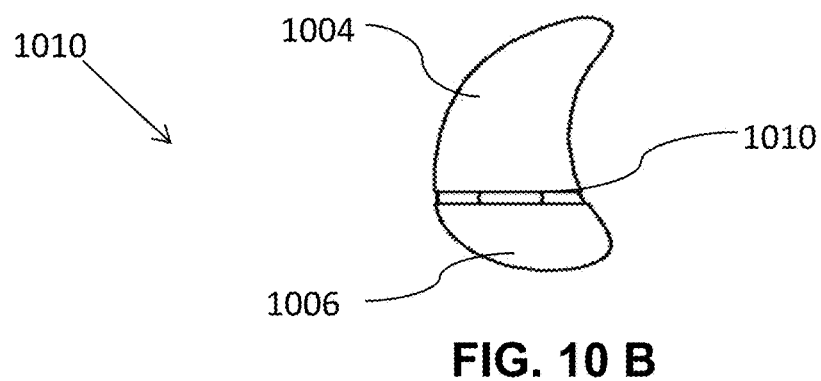

Various profiles and shapes of transdermal drug delivery devices may also be understood from the teachings herein. For example, FIGS. 10A and 10B depict top and bottom perspective views, respectively, of an embodiment of a transdermal drug delivery device 1000. Transdermal drug delivery device 1000 may include any one or more of the features discussed above with reference to the transdermal drug delivery devices 100 and 200, for example. As illustrated, transdermal drug delivery device 1000 includes an upper surface 1002, which may include texturing as discussed above, a first contact surface 1004 and a second contact surface 1006. First contact surface 1004 and second contact surface 1006 are spaced apart by separation channel 1008, and a battery 1010 spans separation channel 1008. In comparison to device 100 of FIG. 1, device 1000 has a different outer profile, including a smaller lobe portion 1012a and a larger lobe portion 1012b. Device 1000 may be advantageously applied to the temple area on a user's face, with smaller lobe portion 1012a positioned near the corner of the user's eye and larger lobe portion 1012b positioned under the user's eye, for example, on the user's cheek. Also in comparison to device 100 of FIG. 1, separation channel 1008 of device 1000 is oriented substantially perpendicular to a longitudinal axis of device 1000.

Figure 11:
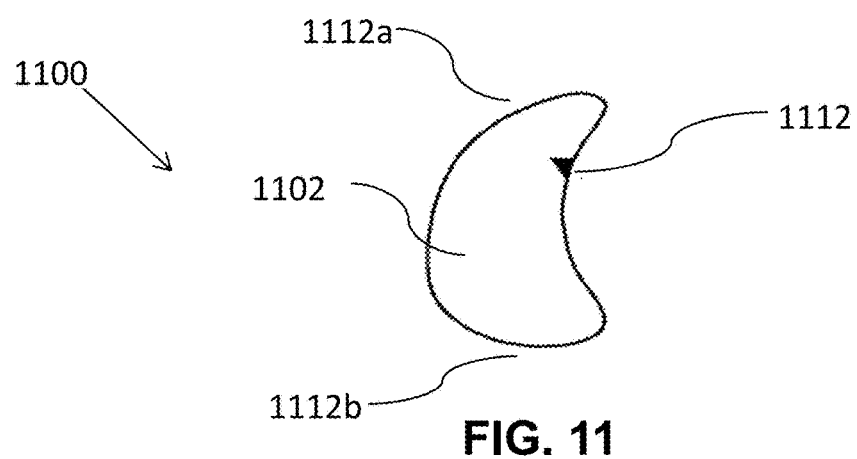
FIG. 11 depicts a top perspective view of an embodiment of a transdermal drug delivery device.

FIG. 11 depicts a top perspective view of an embodiment of a transdermal drug delivery device 1100 having substantially the same outer profile as device 1000, but including a registration feature 1112. Registration feature 1112 may be a printed mark, a notch, a protrusion, or another visual or tactile marker detectable on device 1100. A user or clinician may use registration feature 1112 to correctly position device 1100 by aligning registration feature 1112 with one or more of the user's anatomical features. For example, registration feature 1112 illustrated in FIG. 11 may be positioned so that, when registration feature 1112 is aligned with the outer corner of a user's eye, smaller lobe portion 1112a and larger lobe portion 112b are properly positioned on the user's face. Any of the transdermal drug delivery devices described herein may include one or more registration features to aid in the proper positioning of the devices.

FIGS. 12A-12F illustrate a process for manufacturing a coupling layer for use in a transdermal drug delivery device by illustrating a coupling layer subsequent to various manufacturing operations. For ease of illustration, the coupling layer depicted in FIGS. 12A-12F will be referred to as coupling layer 248 of FIG. 2, but any of the coupling layers disclosed herein may be manufactured using the operations illustrated by FIGS. 12A-12F. In particular, the coupling layers included in the first and second classes of devices, discussed above, may be manufactured using the operations illustrated by FIGS. 12A-12F.

Figure 12:
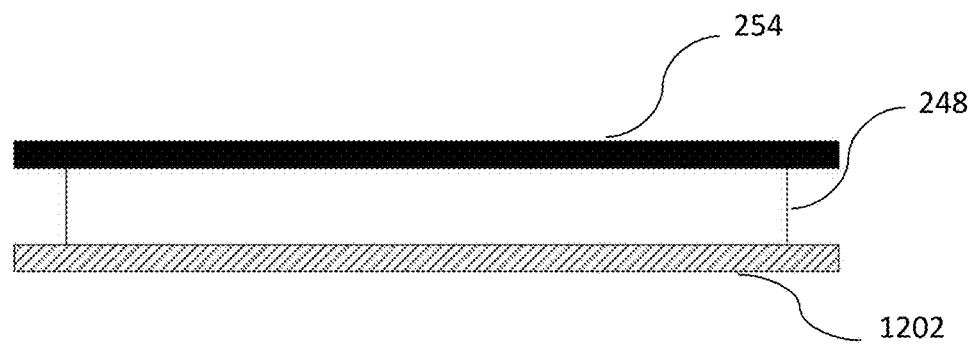
FIGS. 12A-12F illustrate a process for manufacturing a coupling layer for use in a transdermal drug delivery device.
Figure 12:
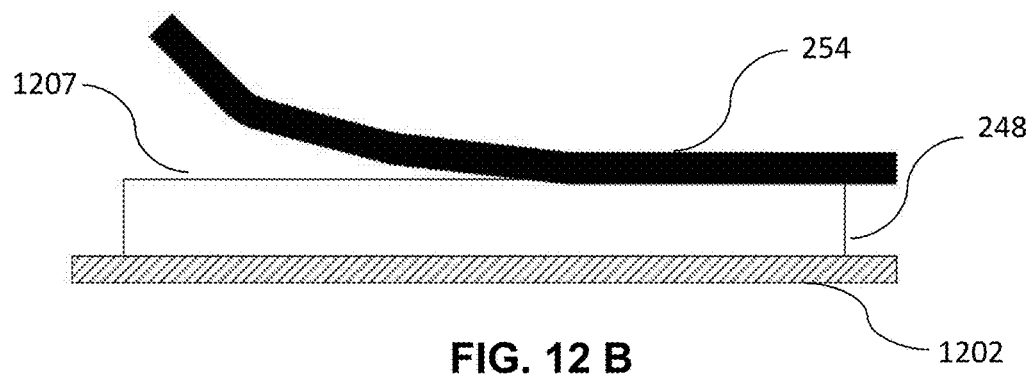
Figure 12:
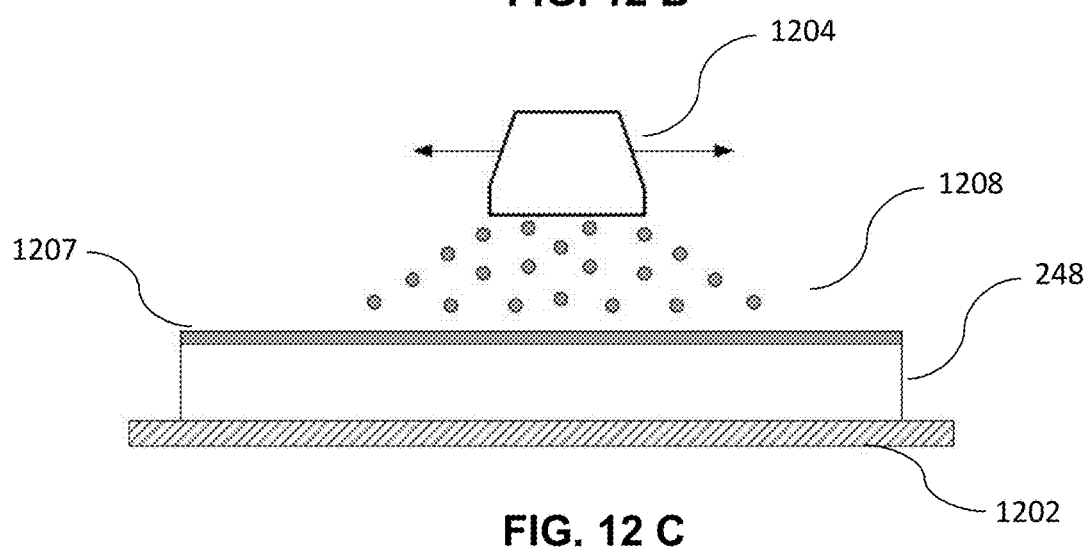
Figure 12:
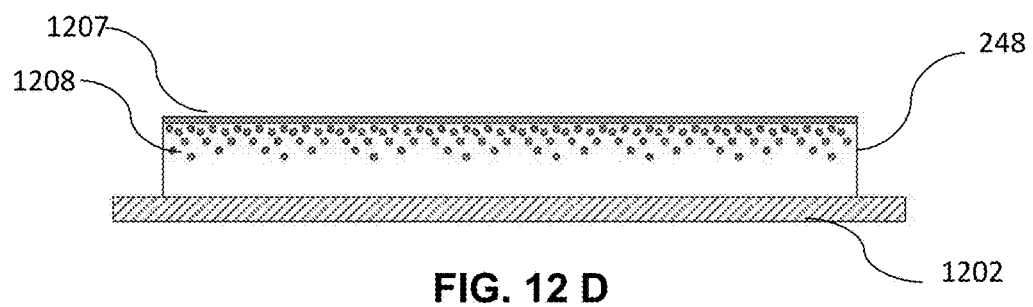
Figure 12:
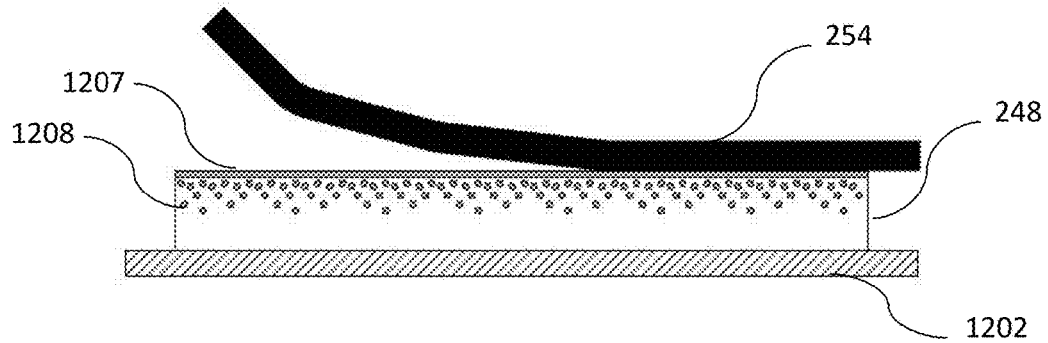
Figure 12:
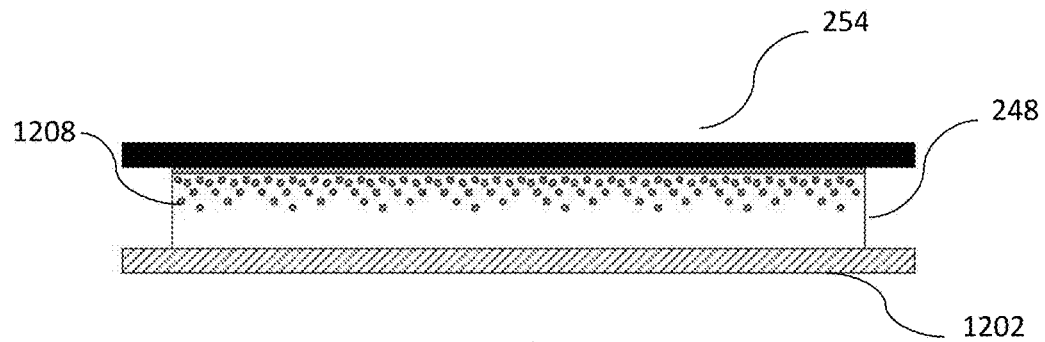

Referring to FIG. 12A, coupling layer 248 is depicted subsequent to an initial manufacturing conversion process in which coupling layer 248 is formed sandwiched between release liner 254 and intermediate liner 1202. In some embodiments, coupling layer 248 is a hydrogel that is distributed onto intermediate liner 1202, distributed by contact with release liner 254, and crosslinked in place by conversion equipment. Coupling layer 248, as depicted in FIG. 12A, could be formed using any gel manufacturing process.

Referring to FIG. 12B, coupling layer 248 is depicted as release liner 254 is peeled from coupling layer 248. Release liner 254 may be peeled in small areas, or in its entirety and set aside. The surface 1207 of coupling layer 248 may be left exposed.

Referring to FIG. 12C, a sprayer 1204 is depicted as spraying a therapeutic agent solution 1208 onto exposed surface 1207 coupling layer 248. Agent solution 1208 may be a solution that includes any therapeutic drug or other agent desired to be included in coupling layer 248. Such agents may include charged agents that will be delivered to the user's tissue upon application of current, or passive agents that will diffuse into the user's tissue when coupling layer 248 contacts the tissue. As illustrated, sprayer 1204 may move over coupling layer 248 to provide even distribution of therapeutic agent solution 1206 as it is sprayed. Upon initial spraying, therapeutic agent solution 1208 may form a layer on exposed surface 1207.

Referring to FIG. 12D, coupling layer 248 is depicted subsequent to a time period during which the therapeutic agent in the therapeutic agent solution 1208 is allowed to migrate into coupling layer 248. The migration of therapeutic agent from therapeutic agent solution 1208 into coupling layer 248 may be passive diffusion and/or may include a temperature or pressure change to speed or otherwise improve the migration. In some embodiments, therapeutic agent from therapeutic agent solution 1208 migrates very little or not at all into coupling layer 248, and may instead dry or otherwise cure largely on surface 1207.

Referring to FIG. 12E, coupling layer 248 is depicted as release liner 254 is reapplied to surface 1207. In some embodiments, the original release liner (removed in the operation illustrated by FIG. 12B) may be discarded, and a different release liner may be applied in the operation illustrated by FIG. 12E. The release liner applied to surface 1207 after therapeutic agent solution 1208 is applied may improve diffusion through of the agent through coupling layer 248. The release liner may also reduce the loss of moisture from coupling layer 248.

Referring to FIG. 12F, coupling layer 248, having agent solution 1208, is depicted sandwiched between release liner 254 and intermediate layer 1202. Subsequent to the operation illustrated by FIG. 12F, coupling layer 248 may be used as any gel layer would, for example, intermediate layer 1202 may be removed and coupled to an electrode of a transdermal drug delivery device, and release liner 254 may be removed prior to the positioning of coupling layer 248 to a user's tissue. Coupling layer 248 may also be handled and transported as a sheet, and layer cut into desired shapes.

The manufacturing process illustrated by FIGS. 12A-12F may provide a number of advantageous over conventional manufacturing processes for forming agent reservoirs in drug delivery devices. Conventionally, the active agents to be delivered by the device are mixed into an uncured gel solution; the mixture is poured onto a liner and cured in place. However, the chemical properties of the agent may affect the ability of the gel to cure, compromising the properties of the gel and sometimes preventing suitable curing from happening at all. Additionally, therapeutic agents may become "trapped" in the matrices formed by cured gels, and thus cannot be effectively delivered to a user. Thus, the choice of agents that can be effectively incorporated into a transdermal drug delivery device has been traditionally limited to those that are compliant with available gels.

Another advantage of some embodiments of the manufacturing process illustrated by FIGS. 12A-12F is that the resulting gel may be more hydrated than convention gels because the agents may be delivered while still in solvent, for example, water, and may have more freedom to move than if they were bound in the gel matrix. Additionally, by applying release liner 254 to surface 1207 before agent solution 1208 has an opportunity to dry, more moisture may be retained in coupling layer 248. In some embodiments, the coupling layer resulting from the manufacturing process illustrated in FIGS. 12A-12F may be more adhesive than conventional drug-impregnated gels, and thus may more readily conform to a user's tissue and maintain contact during wear.

The spraying processes described herein, for example, with reference to FIGS. 12A-12F, and FIG. 13 below, apply the agent to the gel after the gel has cured, thereby avoiding the curing problems that have previously limited transdermal drug delivery. Additionally, by providing the agents to the surface of the gel that will be closest to the user's tissue, the concentration gradient of the therapeutic agent is much higher than if the therapeutic agent were uniformly dispersed through the gel and the concentration is strongest right near the user's tissue. When such a coupling layer is applied to the user's tissue, the speed of passive diffusion may be increased over conventional devices, due to the gradient. Additionally, active delivery may also be improved because therapeutic agent molecules need not travel through the gel to reach the patient's tissue, reducing path resistance and the potential for the agent molecules to get "trapped" in the gel.

The spraying processes described herein also allow a developer of an advantageous therapeutic agent or therapeutic agent solution to keep the composition of that solution confidential, even when manufacturing of the coupling layer is contracted out to a third party, because the therapeutic agent solution can be provided pre-mixed to the third party.

Figure 13:
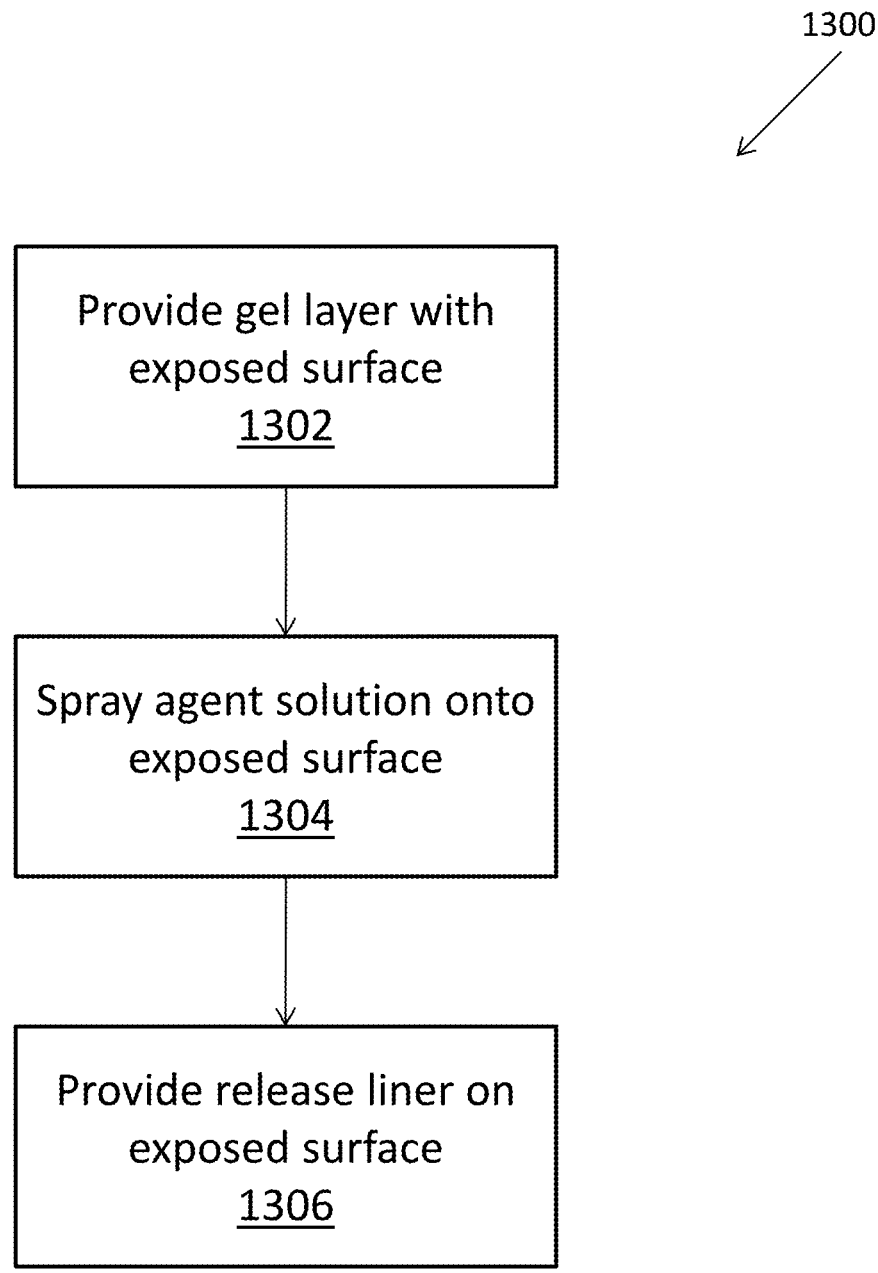
FIG. 13 is a flow diagram of a process for manufacturing a coupling layer for use in a transdermal drug delivery device.

FIG. 13 is a flow diagram 1300 of a process for manufacturing a coupling layer for use in a transdermal drug delivery device. The method of flow diagram 1300 may comport with actions described in connection with FIGS. 12A-12F, in some embodiments. Various operations are described as multiple discrete operations in turn for illustrative purposes; the order of description should not be construed as to imply that these operations are necessarily order dependent.

At 1302, a gel layer may be provided with an exposed surface. The gel layer may be a crosslinked hydrogel. In some embodiments, the surface may be exposed by peeling back a release liner from a cured gel.

At 1304, a therapeutic agent solution may be sprayed onto the exposed surface. The sprayed agent solution may be allowed to dry, cure, and/or diffuse into the gel layer.

At 1306, a release liner may be provided to cover the exposed surface, after the agent solution has been sprayed. The completed coupling layer may then be handled as a sheet, and subsequently incorporated into a transdermal drug delivery device.

In some embodiments, a coupling layer such as coupling layer 248, coupling layer 674 may include a silicone layer instead of a hydrogel or other gel layer. A silicone coupling layer 248 may be flexible and conformal. A silicone coupling layer may be adhesive. A silicone coupling layer may be conductive. A silicone layer may be advantageously washable, allowing a user or clinician to apply a therapeutic agent to the silicone, use the transdermal drug delivery device on the user, remove the device, and rinse off the therapeutic agent prior to the next use. In such embodiments, the therapeutic agent may not be impregnated in the silicone, but may be separately applied, for example, to the silicone surface or to the user's skin via a lotion or cream. Silicone may also advantageously retain its adhesive properties, allowing the transdermal delivery device to repeatedly and consistently adhere to the user's skin. Any of the coupling layers disclosed herein may include both silicone and another coupling material, such as a gel, arranged laterally adjacent, as stacked layers, or in any suitable configuration.

The foregoing is merely illustrative of the principles of the disclosure, and the systems, devices, and methods can be practiced by other than the described embodiments, which are presented for purposes of illustration and not of limitation. Although the embodiments and features described herein are specifically described for use in connection with transdermal delivery systems for delivery of a therapeutic agent, for example, molecules, to a therapy site applied to a portion of the face, it will be understood that all the components, connection mechanisms, adjustable systems, manufacturing methods, and other features outlined below may be combined with one another in any suitable manner and may be adapted and applied to medical devices and procedures for other applications, including, but not limited to delivery of cosmetic agents, pharmaceutical agents, vitamins, biological agents, antibiotics, steroids, antibodies, proteins, peptides, and nutritional supplements.

Variations and modifications will occur to those of skill in the art after reviewing this disclosure. The disclosed features may be implemented, in any combination and sub-combination including multiple dependent combinations and sub-combinations, with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method for delivering a therapeutic molecule to a therapy site, comprising:
    providing a flexible delivery device having a power supply, a first electrode, a second electrode, and a cured gel coupling layer, wherein the first electrode and second electrode are spaced apart by a separation channel;
    spraying a serum containing a therapeutic molecule to an exterior surface of the cured gel coupling layer;
    allowing the serum to at least partially diffuse into the cured gel coupling layer;
    placing the cured gel coupling layer with the serum onto the therapy site to electrically couple the first electrode and the second electrode through a portion of the therapy site, thereby drawing a current from the power supply to deliver the therapeutic molecule to the therapy site;
    removing the flexible delivery device from the therapy site; and
    applying the serum a second time to the exterior layer surface of the cured gel coupling layer, wherein the second application of serum restores at least some adhesive properties of the cured gel coupling layer.

2. The method of claim 1, wherein the molecule has a non-neutral charge.

3. The method of claim 1, wherein the first electrode has a first interface layer integrally coupled to a first conductance layer, wherein the first conductance layer is electrically coupled to a first terminal of the power supply.

4. The method of claim 1, wherein the second electrode has a second interface layer integrally coupled to a second conductance layer, wherein the second conductance layer is electrically coupled to a second terminal of the power supply.

5. The method of claim 1, further comprising flexing the delivery device to conform to the shape of the therapy site.

6. The method of claim 1, further comprising adhering the delivery device to the therapy site by directing a portion of the cured gel directly on the therapy site.

7. The method of claim 1, wherein the power supply, first electrode, and second electrode are coupled to an upper base layer.

8. The method of claim 1, wherein the first electrode has a first coupling layer and the second electrode has a second coupling layer, wherein the first coupling layer and second coupling layer contact the therapy site when the first electrode and second electrode are placed on the therapy site.

9. The method of claim 1, further comprising cleaning the exterior layer surface of the cured gel coupling layer prior to applying the serum a second time.

10. The method of claim 1, wherein a release liner is immediately applied to the cured-gel layer after the spraying step, such that more moisture may be retained in the cured gel coupling layer, and the cured gel coupling layer has increased adhesive properties that more readily conform to a user's tissue and maintain contact during wear.

11. The method of claim 1, further comprising placing the cured gel coupling layer after the application of serum a second time onto the therapy site or a second therapy site to electrically couple the first electrode and the second electrode through a portion of the therapy site or second therapy site, thereby drawing current from the power supply to deliver the therapeutic molecule to the therapy site.

* * * * *